US010561852B2

(12) United States Patent
Murphy et al.

(10) Patent No.: US 10,561,852 B2
(45) Date of Patent: Feb. 18, 2020

(54) SYSTEMS AND METHODS FOR PROVIDING RAPID MEDICAL CARE

(71) Applicant: ZOLL Medical Corporation, Chelmsford, MA (US)

(72) Inventors: Jim Murphy, Bedford, MA (US); Charles E. Sawyer, Jr., Sudbury, MA (US); Melissa M. Dascoli, Wakefield, MA (US); Bruce Edwards, Marlborough, MA (US); Tim Stever, Lowell, MA (US); Allan Scott Baucom, Boxboro, MA (US); Lawrence W. Peck, Andover, MA (US); Tyler Harrington, Westford, MA (US); Gary A. Freeman, Waltham, MA (US); Christine O'Toole, West Roxbury, MA (US); Donald Joseph Paradis, West Townsend, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 75 days.

(21) Appl. No.: 15/433,047

(22) Filed: Feb. 15, 2017

(65) Prior Publication Data

US 2017/0246466 A1    Aug. 31, 2017

Related U.S. Application Data

(60) Provisional application No. 62/300,419, filed on Feb. 26, 2016.

(51) Int. Cl.
*A61N 1/39* (2006.01)
(52) U.S. Cl.
CPC ......... *A61N 1/3925* (2013.01); *A61N 1/3975* (2013.01); *A61N 1/3993* (2013.01)

(58) Field of Classification Search
CPC ... A61N 1/3925; A61N 1/3904; A61N 1/3975
See application file for complete search history.

(56) References Cited

U.S. PATENT DOCUMENTS 5,645,571 A    7/1997   Olson et al.
5,749,913 A *  5/1998   Cole ................ G16H 15/00
                                              607/59

(Continued)

FOREIGN PATENT DOCUMENTS

EP         761255 A1    3/1997
WO      2014097035 A1    6/2014

OTHER PUBLICATIONS

Association for the Advancement of Medical Instrumentation, ANSI/AAMI DF80:2003, Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

*Primary Examiner* — Joseph M Dietrich
(74) *Attorney, Agent, or Firm* — Finch & Maloney PLLC

(57) ABSTRACT

In various embodiments, the presently described methods, apparatus, and systems can facilitate decreasing a boot time of a medical device, e.g., an amount of time between when a medical device or system is first turned on or powered on and when the medical device or system is ready to perform its intended function. In some embodiments, the present disclosure can also facilitate conducting tests on the functionality of various operational circuits shortly or immediately after the device/system has been activated. In some cases, the emergency medical devices/systems can report on the status or functionality of operational circuits even before the emergency medical device is fully booted up and ready to perform some or all of its intended functions.

19 Claims, 12 Drawing Sheets

(56) References Cited

U.S. PATENT DOCUMENTS

| | | | |
|---|---|---|---|
| 5,879,374 | A | 3/1999 | Powers et al. |
| 5,899,925 | A | 5/1999 | Ochs et al. |
| 5,919,212 | A | 8/1999 | Olson et al. |
| 6,304,780 | B1 | 10/2001 | Owen et al. |
| 6,681,003 | B2 | 1/2004 | Linder et al. |
| 7,627,372 | B2 | 12/2009 | Vaisnys et al. |
| 8,140,154 | B2 | 3/2012 | Donnelly et al. |
| 8,224,441 | B2 | 7/2012 | Vaisnys et al. |
| 8,319,632 | B1 | 11/2012 | Vaisnys et al. |
| 8,904,214 | B2 | 12/2014 | Volpe et al. |
| 2003/0032988 | A1 | 2/2003 | Fincke |
| 2006/0136000 | A1 | 6/2006 | Bowers |
| 2013/0013014 | A1* | 1/2013 | Donnelly ............ A61N 1/39 607/7 |
| 2014/0379255 | A1 | 12/2014 | Johnson |
| 2015/0035654 | A1* | 2/2015 | Kaib ............ A61N 1/3925 340/10.51 |
| 2015/0039053 | A1 | 2/2015 | Kaib et al. |
| 2016/0274162 | A1 | 9/2016 | Freeman et al. |

\* cited by examiner

700

702: Header
704: "Call for Help" Block Image
706: "Unit Failed" Ribbon Image
708: "Unit OK" Ribbon Image
710: "Battery Test in Progress" Ribbon Image
712: "Unit Failed" Audio Prompt
714: "Unit OK" Audio Prompt
716: Data integrity check

FIG. 7

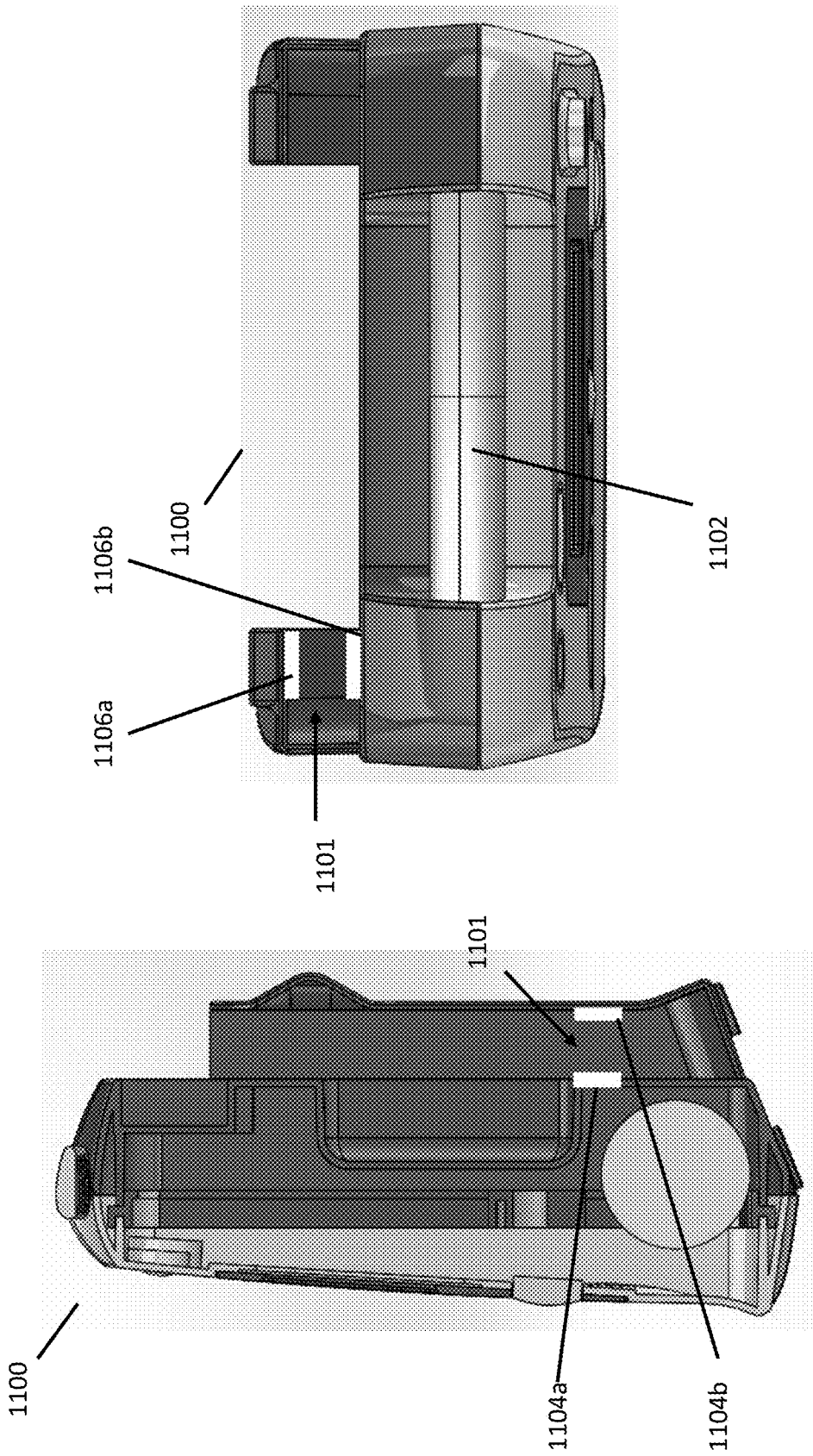

SYSTEMS AND METHODS FOR PROVIDING RAPID MEDICAL CARE

CROSS REFERENCE TO RELATED APPLICATIONS

This application claims priority to U.S. Provisional Application No. 62/300,419, filed on Feb. 26, 2016, entitled "SYSTEMS AND METHODS FOR PROVIDING RAPID MEDICAL CARE," which is incorporated herein by reference.

TECHNICAL FIELD

Embodiments of the present disclosure relate generally to electronic devices, and more particularly, to methods and systems for facilitating rapid medical care.

BACKGROUND

For some devices, for example, emergency medical devices, it is often desirable to use these devices within a short time period after turning them on. Furthermore, users of such devices may prefer to receive an indication that the device is operating properly before starting to perform necessary medical activities. In the context of an emergency medical device such as an Automatic External Defibrillator (AED), for example, a user such as an EMS technician or bystander caregiver may require assurance that the device is starting up normally and that important subsystems are functioning properly within a few seconds of turning it on before initiating resuscitative care.

SUMMARY

According to example 1, the present disclosure is directed at a medical system comprising: a plurality of operational circuits; at least one processor coupled to the plurality of operational circuits, the at least one processor configured to: initiate, when the medical system is activated, a boot process for the medical system, wherein the boot process comprises a first phase and a second phase, wherein the first phase is executed prior to the second phase; execute, as part of the first phase of the boot process, a first set of tests, wherein each test from the first set of tests is configured to test functionality of at least some of the operational circuits; provide an indication regarding usability of the medical system prior to completion of the boot process; and after implementing the first set of tests, execute the second phase of the boot process.

According to example 2, the present disclosure is directed at the medical system of example 1, wherein the at least one processor is capable of executing multiple process threads.

According to example 3, the present disclosure is directed at the medical system of any of examples 1-2, wherein the first phase does not trigger the execution of multiple process threads, and the second phase triggers the execution of multiple process threads.

According to example 4, the present disclosure is directed at the medical system of any of examples 1-3, wherein the at least one processor is further configured to execute, as part of the second phase of the boot process, a second set of tests, wherein each test from the second set of tests is configured to test the functionality of at least some of the operational circuits.

According to example 5, the present disclosure is directed at the medical system of any of examples 1-4, wherein the at least one processor comprises a first processor and a second processor, the first processor including a processor core.

According to example 6, the present disclosure is directed at the medical system of any of examples 1-5, wherein the processor core is configured to execute the first set of tests by fetching a result of a self-test conducted by the second processor.

According to example 7, the present disclosure is directed at the medical system of any of examples 1-6, wherein the first set of tests include a power on self-test conducted by the at least one processor.

According to example 8, the present disclosure is directed at the medical system of any of examples 1-7, wherein the first processor is configured to implement a general purpose operating system; and the second processor is configured to implement a real-time operating system.

According to example 9, the present disclosure is directed at the medical system of any of examples 1-8, wherein the operational circuits comprise a defibrillator circuit configured to deliver a therapeutic electric shock to a patient; and the first set of tests comprise a test on the defibrillator circuit.

According to example 10, the present disclosure is directed at the medical system of any of examples 1-9, wherein the operational circuits comprise an input circuit configured to instruct the defibrillator circuit to deliver the therapeutic electric shock; and the first set of tests comprise a test on the input circuit.

According to example 11, the present disclosure is directed at the medical system of any of examples 1-10, wherein the operational circuits comprise a battery; and the second set of tests comprise a test on the functionality of the battery.

According to example 12, the present disclosure is directed at the medical system of any of examples 1-11, wherein the operational circuits comprise an inter-component communication circuit associated with a communication circuit driver; and the processor core is configured to execute the first set of tests by utilizing the inter-component communication circuit before loading the associated communication circuit driver.

According to example 13, the present disclosure is directed at the medical system of any of examples 1-12, wherein the inter-component communication circuit is at least one of an Inter-Integrated Circuit (I2C) and a Universal Asynchronous Receiver/Transmitter (UART).

According to example 14, the present disclosure is directed at the medical system of any of examples 1-13, wherein the operational circuits comprise a user interface output device associated with an output device driver; and the processor core is configured to report the results associated with the first set of tests by utilizing the user interface output device before loading the output device driver.

According to example 15, the present disclosure is directed at the medical system of any of examples 1-14, wherein the user interface provides the indication regarding usability of the medical system prior to completion of the boot process.

According to example 16, the present disclosure is directed at the medical system of any of examples 1-15, wherein the user interface output device is at least one of an audio speaker and a video display.

According to example 17, the present disclosure is directed at the medical system of any of examples 1-16, wherein the video display is configured to display an initial image to provide the indication regarding usability of the medical system prior to completion of the boot process.

According to example 18, the present disclosure is directed at the medical system of any of examples 1-17, wherein the audio speaker is configured to announce a prompt to provide the indication regarding usability of the medical system prior to completion of the boot process.

According to example 19, the present disclosure is directed at the medical system of any of examples 1-18, further comprising a defibrillator housing, the defibrillator housing containing the plurality of operational circuits.

According to example 20, the present disclosure is directed at a medical system comprising: a plurality of operational circuits; a plurality of system resources, each system resource being associated with a system resource driver; at least one processor coupled to the plurality of operational circuits and the plurality of system resources, the at least one processor configured to: implement a first set of tests on the functionality of at least some of the operational circuits by utilizing at least some of the system resources before the system resource drivers associated with the at least some system resources have been loaded; provide an indication regarding usability of the medical system based on the first set of tests; and after implementing the first set of tests, loading the system resource drivers associated with the plurality of system resources.

According to example 21, the present disclosure is directed at the medical system of any of examples 1-20, wherein the at least one processor is configured to provide the indication regarding usability of the medical system prior to loading of the system resource drivers associated with the plurality of system resources.

According to example 22, the present disclosure is directed at the medical system of any of examples 1-21, wherein the at least one processor is further configured to implement a second set of tests on the functionality of at least some of the operational circuits after loading the system resource drivers associated with the plurality of system resources.

According to example 23, the present disclosure is directed at the medical system of any of examples 1-22, the at least one processor comprises a first processor and a second processor; and the at least one processor is configured to implement the first set of tests by causing the first processor to fetch a result of a self-test conducted by the second processor.

According to example 24, the present disclosure is directed at the medical system of any of examples 1-23, wherein the at least some system resources comprise at least one of an Inter-Integrated Circuit (I2C), a Universal Asynchronous Receiver/Transmitter (UART), an audio speaker, and a video display.

According to example 25, the present disclosure is directed at the medical system of any of examples 1-24, wherein the operational circuits comprise a defibrillator circuit configured to deliver a therapeutic electric shock to a patient; and the first set of tests comprise a test on the defibrillator circuit.

According to example 26, the present disclosure is directed at the medical system of any of examples 1-25, wherein the operational circuits comprise an input circuit configured to instruct the defibrillator circuit to deliver the therapeutic electric shock; and the first set of tests comprise a test on the input circuit.

According to example 27, the present disclosure is directed at the medical system of any of examples 1-26, further comprising a defibrillator housing, the defibrillator housing containing the plurality of operational circuits.

According to example 28, the present disclosure is directed at a medical system comprising: at least one sensor configured to detect an indication of activity; an activation switch configured for actuation by a user of the medical system; at least one processor in communication with the at least one sensor and the activation switch, configured to: upon detection of the indication of the activity from the at least one sensor, cause the medical system to transition from a sleep state to a standby state; and upon detection of an actuation of the activation switch, cause the medical system to transition to a fully activated state, wherein a first time period required for the medical system to transition from the standby state to the fully activated state is shorter than a second time period required for the medical system to transition from the sleep state to the fully activated state.

According to example 29, the present disclosure is directed at the medical system of any of examples 1-28, wherein the at least one sensor comprises an accelerometer configured to measure an acceleration associated with the medical system.

According to example 30, the present disclosure is directed at the medical system of any of examples 1-29, wherein the indication of activity comprises the measured acceleration exceeding a predetermined acceleration threshold.

According to example 31, the present disclosure is directed at the medical system of any of examples 1-30, wherein the medical system is configured to calculate a displacement associated with the medical system based on the acceleration measured by the accelerometer; and the indication of activity comprises the calculated displacement exceeding a predetermined displacement threshold.

According to example 32, the present disclosure is directed at the medical system of any of examples 1-31, wherein the at least one sensor comprises an orientation sensor configured to measure an orientation associated with the medical system; and the indication of activity comprises the orientation sensor measuring a change in orientation associated with the medical system.

According to example 33, the present disclosure is directed at the medical system of any of examples 1-32, wherein the medical system is configured to calculate a displacement associated with the medical system based on the acceleration measured by the accelerometer; and the indication of activity comprises the measured acceleration exceeding a predetermined acceleration threshold and the calculated displacement exceeding a predetermined displacement threshold.

According to example 34, the present disclosure is directed at the medical system of any of examples 1-33, wherein the at least one sensor comprises a power sensor configured to determine whether the medical system is connected to a power source; and the indication of activity comprises the power sensor detecting that the medical system is at least one of connected and disconnected to the power source.

According to example 35, the present disclosure is directed at the medical system of any of examples 1-34, wherein the at least one sensor comprises a light sensor configured to measure a light level; and the indication of activity comprises the measured light level exceeding a pre-determined threshold.

According to example 36, the present disclosure is directed at the medical system of any of examples 1-35, wherein the at least one sensor comprises an ultrasound sensor configured to detect a distance to a neighboring surface; and the indication of activity comprises a change in the detected distance.

According to example 40, the present disclosure is directed at the medical system of any of examples 1-36, wherein the medical system further comprises a handle; the at least one sensor comprises a capacitance sensor configured to measure a capacitance associated with the handle; and the indication of activity comprises the capacitance sensor measuring a capacitance.

According to example 41, the present disclosure is directed at the medical system of any of examples 1-37, wherein the medical system further comprises a plurality of operational circuits; and the medical system is configured to verify the functionality of at least some of the plurality of operational circuits while in the standby state.

According to example 42, the present disclosure is directed at the medical system of any of examples 1-38, wherein the operational circuits comprise a defibrillator circuit configured to deliver a therapeutic electric shock to a patient; and the medical system is configured to verify the functionality of the defibrillator circuit while in the standby state.

According to example 43, the present disclosure is directed at the medical system of any of examples 1-39, further comprising a defibrillator housing, the defibrillator housing containing the plurality of operational circuits.

According to example 44, the present disclosure is directed at the medical system of any of examples 1-40, further comprising electrodes initially located in a holster, wherein the at least one sensor is configured to detect whether the electrodes have been removed from the holster.

According to example 45, the present disclosure is directed at a medical device comprising: a housing; at least one motion sensor coupled to the housing and configured to sense motion of the device; an operational circuit configured to administer medical treatment to a patient; and at least one processor in communication with the at least one motion sensor, the at least one processor configured to: cause the medical system to transition from a sleep state to at least one of a standby state and a fully activated state based on the sensed motion, and cause the operational circuit to administer the medical treatment.

According to example 46, the present disclosure is directed at the medical system of any of examples 1-42, wherein the at least one motion sensor includes an accelerometer.

According to example 47, the present disclosure is directed at the medical system of any of examples 1-43, wherein the operational circuit is configured to provide a defibrillating shock to the patient.

According to example 48, the present disclosure is directed at a medical system comprising: a processor configured to: run at a first clock speed associated with a first mean time before failure (MTBF) for a startup time period after being activated from a sleep state; and run at a second clock speed associated with a second MTBF after the expiration of the startup time period, wherein both the first clock speed and the second clock speed are approved clock speeds for the processor; wherein the first MTBF is shorter than the second MTBF.

According to example 49, the present disclosure is directed at the medical system of any of examples 1-45, wherein the processor is configured to execute boot code while running at the first clock speed.

According to example 50, the present disclosure is directed at the medical system of any of examples 1-46, wherein the first clock speed is greater than 25% higher than the second clock speed.

According to example 51, the present disclosure is directed at the medical system of any of examples 1-47, further comprising a heat sensor configured to measure a die temperature.

According to example 52, the present disclosure is directed at the medical system of any of examples 1-48, wherein the startup time period is determined at least in part by the die temperature measured by the heat sensor.

According to example 53, the present disclosure is directed at the medical system of any of examples 1-49, further comprising a defibrillator circuit configured to deliver a therapeutic electric shock to a patient.

BRIEF DESCRIPTION OF THE DRAWINGS

FIG. 7 is a logical block diagram illustrating at least part of the contents of a Pre-Flight Data Store, according to some embodiments.

FIG. 11A, FIG. 11B and FIG. 11C illustrate an automated external defibrillator, according to some embodiments.

Figure 1:
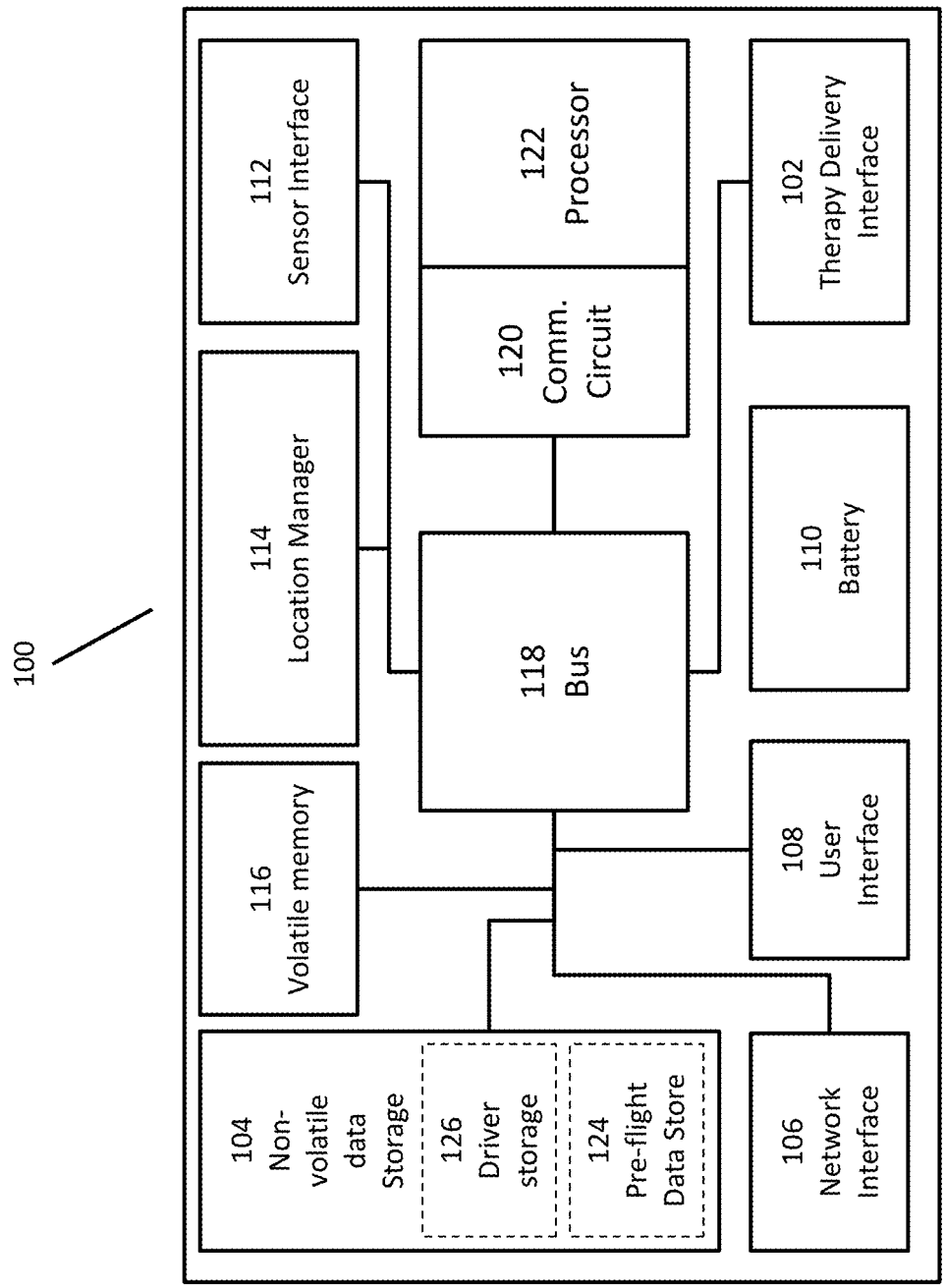
FIG. 1 illustrates a medical device controller, according to some embodiments.

While aspects of the present disclosure are amenable to various modifications and alternative forms, specific embodiments have been shown by way of example in the drawings and are described in detail below. The intention, however, is not to limit the invention to the particular embodiments described. On the contrary, the present disclosure is intended to cover all modifications, equivalents, and alternatives falling within the scope of the invention as provided by the appended claims.

DETAILED DESCRIPTION

Emergency medical devices or systems are often used in situations where a rapid response can be critical to ensuring a successful outcome. In the example of cardiac arrest, the longer the patient is down without having received emergency care, such as cardiopulmonary resuscitation (CPR) or other treatment(s), the less likely the patient will survive. Despite this finding, when faced with such situations, users of emergency medical devices (e.g., AEDs) may have a tendency to require a certain level of assurance, within a relatively short time after turning on the device, that the device is or will be operating properly, even if the device is not yet fully booted and/or ready to function. Otherwise, the user may be preoccupied with concern as to whether the device is properly functioning and, hence, may withhold resuscitative care. However, once the user receives such assurance, even if the device is not yet fully functional, the user is then more likely to start engaging in parallel resuscitative activities, such as cutting clothes off of a patient, placing electrodes on the patient's body, and/or calling for help. Accordingly, it may be advantageous for the device to provide some indication to the user of its ability to function properly prior to achieving the actual functionality, so that the user is put at ease as to whether the device works. The user may then be confident in moving on to commence, continue or otherwise provide resuscitative efforts.

In various embodiments, it may be desirable to decrease a boot time, e.g., an amount of time between when a medical device or system is first turned on or powered on and when the medical device or system is ready to perform its intended function. However, as medical devices or systems become more complicated and embody a greater number of features, more complex software and/or hardware can be required to support all of the medical devices' or systems' functions. As a result, added features and functionalities can contribute to slowing down the overall boot times of emergency medical devices/systems, from power-on to full functionality. In some embodiments, the techniques described herein are directed at reducing the user-perceived boot time of emergency medical devices or systems. This increases the likelihood that users will provide resuscitative care to the patient while the emergency medical device(s) are able to perform their intended functions, for example, shortly after activation.

In some situations, it may also be desirable to enable emergency medical devices/systems to conduct tests on the functionality of various operational circuits shortly or immediately after the device/system has been activated. In some embodiments, the techniques described herein are directed at systems, apparatus and methods that enable emergency medical devices/systems to verify and/or report on the functionality of key operational circuits within a short time after the device/system has been activated. In some cases, the emergency medical devices/systems can report on the status or functionality of operational circuits even before the emergency medical device is fully booted up and ready to perform some or all of its intended functions. As noted herein, early status or functionality reporting can give an operator assurance that the device is ready or will soon be ready to perform its functions, which allows the operator to turn to other, important tasks (e.g., cutting off extraneous clothing, treating traumatic injuries, contacting authorities for help, administering CPR, etc.) while the device is booting up in parallel.

FIG. 1 illustrates a medical device controller 100 that is configured to monitor a patient, monitor the patient's environment, or administer a treatment to a patient. The medical device controller 100 may, for example, be configured for use in a wearable defibrillator or an Automated External Defibrillator (AED). As shown in FIG. 1, the medical device controller 100 can include a network interface 106, a user interface 108, a battery 110, a bus 118, non-volatile data storage 104 having a driver storage section 126 and a pre-flight data store 124, volatile memory 116, a location manager 114, a sensor interface 112, a therapy delivery interface 102, a communication circuit 120, and a processor 122. Medical device controller 100 can also be modified to omit any of the above components, or to include additional components.

In this illustrated example, the battery 110 is a rechargeable 3-cell 2200 mAh lithium ion battery pack that can provide electrical power to the other device components with a minimum 24-hour runtime between charges. It is appreciated that the battery capacity, runtime, and type (e.g., lithium ion, nickel-cadmium, or nickel-metal hydride) can be changed to best fit the specific application of the medical device controller 100.

According to the embodiment illustrated in FIG. 1, the processor 122 is coupled to the sensor interface 112, the therapy delivery interface 102, the non-volatile data storage 104, the network interface 106, the user interface 108, the location manager 114, and the volatile memory 116 via the communication circuit 120 and the bus 118. Some or all of the peripheral devices disclosed in FIG. 1 can also be connected directly with the processor 122, thus bypassing one or both of bus 118 and communication circuit 120. The processor 122 can perform a series of instructions that result in manipulated data which are stored in and retrieved from the non-volatile data storage 104 and/or the volatile memory 116. According to a variety of embodiments, the processor 122 is a commercially available processor such as a processor manufactured or provided by Texas Instruments, Intel, AMD, Sun, IBM, Motorola, Freescale, and ARM Holdings. However, the processor 122 may be any type of processor, multi-processor or controller, whether commercially available or specially manufactured. For instance, according to one embodiment, the processor 122 may include a power conserving processor arrangement such as described in issued U.S. Pat. No. 8,904,214, titled "SYSTEM AND METHOD FOR CONSERVING POWER IN A MEDICAL DEVICE," filed Jul. 9, 2010 (hereinafter the "'096 application"), which is hereby incorporated herein by reference in its entirety. In another embodiment, the processor 122 is an Intel® PXA270.

In some embodiments, the processor 122 can comprise two or more processors and/or two or more processor cores (e.g., processor able to execute multiple processing strings or threads in parallel and/or intermittently). At least some of these processors and/or processor cores can be configured to execute a conventional real-time operating system (RTOS), such as QNX, VxWorks, and/or OSE. At least some of these processors and/or processor cores can also be configured to execute a conventional general-purpose operating system (GPOS), such as BSD or BNU/Linux. In these embodiments, the RTOS may provide platform services to application software, such as some embodiments of the location manager 114 or the therapy delivery interface 102. These platform services may include inter-process and network communication, file system management and standard database manipulation. One or more of many operating systems may be used, and embodiments are not limited to any particular operating system or operating system characteristic.

The processor 122 can be coupled to other components in the medical device controller 100 via a communication circuit 120 and a bus 118. Communication circuit 120 can be a circuit that converts or translates data, thereby facilitating communications between the processor 122 and other system components via bus 118. In some embodiments, communication circuit 120 can be a universal asynchronous receiver/transmitter (UART) which translates data between parallel and serial forms. Bus 118 can be a computer bus that communicably couples peripherals with processor 122. In some embodiments, bus 118 can be an Inter-Integrated Circuit (I2C) bus, a Serial Peripheral Interface (SPI) bus, an RS-485 bus, a Controller Area Network (CAN) bus, a Universal Serial Bus (USB), or other type of bus. In some embodiments, other components in the medical device controller 100 can also be connected to processor 122 in other ways, including ways that bypass one or both of bus 118 and communication circuit 120. Or, multiple buses similar to bus 118 may be instantiated. Although FIG. 1 depicts only one communication circuit 120 and one bus 118, it is to be appreciated that some embodiments may contain multiple communication circuits 120 and/or buses 118, which may or may not be of the same type. For instance, some embodiments of medical device controller 100 may include two or more buses 118. The buses may all be the same type of bus (e.g., an I2C bus), or may be different types of buses.

The non-volatile data storage 104 can include a computer readable and writeable non-volatile data storage medium configured to store non-transitory instructions and data. Non-volatile data storage 104 can include any device for storing non-volatile data with sufficient throughput and storage capacity to support the functions described herein, and can include driver storage section 126 and pre-flight data store 124, both of which are described in greater detail below.

Volatile memory 116 can be any type of volatile memory that supports the operations of processor 122 during execution of its instructions. In some embodiments, the processor memory includes a relatively high-performance, volatile, random access memory such as dynamic random access memory (DRAM), static memory (SRAM) or synchronous DRAM.

According to several embodiments, the processor 122 can cause data to be read from the nonvolatile data storage 104 into volatile memory 116 prior to processing the data. In these embodiments, the processor 122 can copy the data from the volatile memory 116 to the non-volatile data storage 104 after processing is complete. A variety of components can manage data movement between the non-volatile storage medium and the processor memory and embodiments are not limited to particular data management components. Further, embodiments are not limited to a particular memory, memory system or data storage system. The instructions stored on the data storage 104 can include executable programs or other code that can be executed by the processor 122. The instructions may be persistently stored as encoded signals, and the instructions may cause the processor 122 to perform the functions described herein. The non-volatile data storage 104 also can include information that is recorded on or in the medium, and this information may be processed by the processor 122 during execution of instructions. The medium can, for example, be optical disk, magnetic disk or flash memory, among others, and can be permanently affixed to, or removable from, the medical device controller 100.

In some embodiments, the medical device controller 100 can comprise an optional location manager 114. The location manager 114 can be configured to determine the location of the medical device, and can be implemented using hardware or a combination of hardware and software. For instance, in one embodiment, the location manager 114 is implemented as a software component that is stored within the data storage 104 and executed by the processor 122. In this embodiment, the instructions included in the location manager 114 program the processor 122 to determine the location of the medical device. In other embodiments, location manager 114 can be an application-specific integrated circuit (ASIC) that is coupled to the processor 122 and tailored to determine the location of the medical device. In some embodiments, the location manager may employ suitable displacement logic, as known to those of skill in the art, for example, in conjunction with the network interface 106, to provide location services to emergency medical personnel (e.g., advanced life support personnel) prior to arrival on site. Thus, embodiments of the location manager 114 are not limited to a particular hardware or software implementation.

As shown in FIG. 1, the medical device controller 100 can also optionally include several system interface components, such as a therapy delivery interface 102, a network interface 106, and a sensor interface 112. Each of these system interface components can be configured to exchange, i.e., send or receive, data with one or more specialized devices that can be located within the housing of the medical device controller 100 or elsewhere. The components used by the interfaces 102, 106, and 112 can include hardware components, software components, or a combination of both. Within each interface, these components physically and logically couple the medical device controller 100 to the specialized devices. This physical and logical coupling enables the medical device controller 200 to communicate with and/or, in some instances, power or control the operation of the specialized devices. These specialized devices can include, for example, physiological sensors, therapy delivery devices, and computer networking devices.

According to various embodiments, the hardware and software components of the interfaces 102, 106, and 112 implement a variety of coupling and communication techniques. In some embodiments, the interfaces 102, 106, and 112 use leads, cables or other wired connectors as conduits to exchange data between the medical device controller 100 and specialized devices. In other embodiments, the interfaces 102, 106, and 112 communicate with specialized devices using wireless technologies such as radio frequency or infrared technology. The software components included in the interfaces 102, 106, and 112 enable the processor 122 to communicate with specialized devices. These software components can include elements such as objects, executable code, and populated data structures. Together, these software components provide software interfaces through which the processor 122 can exchange information with specialized devices. Moreover, in at least some embodiments where one or more specialized devices communicate using analog signals, the interfaces 102, 106, and 112 further include components configured to convert analog information into digital information, and vice versa, to enable the processor 122 to communicate with specialized devices.

As discussed above, the system interface components 102, 106, and 112 shown in the embodiment of FIG. 1 support different types of specialized devices. For instance, the components of the sensor interface 112 can couple the processor 122 to one or more physiological sensors such as body temperature sensors, respiration monitors, electrocardiogram (ECG) sensing electrodes, blood oxygen sensors, and heartbeat sensors, and/or one or more environmental sensors such as atmospheric thermometers, airflow sensors, video sensors, audio sensors, accelerometers, GPS locators, infrared sensors, magnetic sensors, and hygrometers, amongst others. In these embodiments, the sensor may include sensors with a relatively low sampling rate, such as wireless sensors.

The components of the therapy delivery interface 102 can couple one or more therapy delivery devices, such as capacitors, defibrillator electrodes, pacing electrodes, or mechanical chest compression devices, respirators, or medication delivery devices to the processor 122. It is appreciated that the functionality of the therapy delivery interface 102 can be incorporated into the sensor interface 112 to form a single interface coupled to the processor 122. In addition, the components of the network interface 106 can couple the processor 122 to a computer network via a networking device, such as a bridge, router, or hub. According to a variety of embodiments, the network interface 106 can support a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, IDP, DTN, HTTP, FTP, SNMP, CDMA, NMEA, and GSM. It is appreciated that the network interface 106 of the medical device controller 100 can enable communication between other medical device controllers within an appropriate range or, for certain instances (e.g., TCP/IP), an unlimited range.

To ensure data transfer is secure, in some embodiments, the medical device controller 100 can transmit data via the network interface 106 using a variety of security measures including, for example, TLS, SSL or VPN. In other embodiments, the network interface 106 can include both a physical interface configured for wireless communication and a physical interface configured for wired communication. According to various embodiments, the network interface 106 can enable communication between the medical device controller 100 and a variety of personal electronic devices including computer enabled glasses and earpieces. In one embodiment, the network interface 106 is also capable of transmitting and/or receiving information to assist in medical device location determination. Exemplary methods in which the network interface 106 can be used to assist in medical device location determination is described in US Patent Application Publication No. 2014/0379255, titled "SYSTEMS AND METHODS OF DETERMINING LOCATION USING A MEDICAL DEVICE," published on Dec. 25, 2014, which is incorporated herein by reference in its entirety.

Thus, the various system interfaces incorporated in the medical device controller 100 allow the device to interoperate with a wide variety of devices in various contexts. For instance, some embodiments of the medical device controller 100 are configured to perform a process of sending critical events and data to a centralized server via the network interface 106. An illustration of a process in accord with these embodiments is disclosed in U.S. Pat. No. 6,681,003, titled "DATA COLLECTION AND SYSTEM MANAGEMENT FOR PATIENT-WORN MEDICAL DEVICES," and issued on Jan. 20, 2004, which is incorporated herein by reference in its entirety.

Various components in FIG. 1 are optional and may not be included in every embodiment. For instance, a heart rate monitor may employ the medical device controller 100 to issue alarms but may not include a therapy delivery interface 102 to treat cardiac abnormalities. Similarly, an ambulatory defibrillator may include the medical device controller 100 to provide alarm functionality but may not include a network interface 106, where, for example, the ambulatory defibrillator is designed to rely on the user interface 108 to announce alarms.

The user interface 108 shown in FIG. 1 can include a combination of hardware and software components that allow the medical device controller 100 to communicate with an external entity, such as a patient or other user. These components may be configured to receive information from actions such as physical movement, verbal intonation or thought processes. In addition, the components of the user interface 108 can provide information to external entities. Examples of the components that may be employed within the user interface 108 include keyboards, mouse devices, trackballs, microphones, electrodes, touch screens, printing devices, display screens, and speakers. In some embodiments, the electrodes include an illuminating element, such as an LED. In other embodiments, the printing devices include printers capable of rendering visual or tactile (Braille) output.

In some embodiments, some or all of the components in the medical device controller 100 can be associated with one or more drivers, or software instructions for enabling the processor 122 to operate and/or control each peripheral. For instance, user interface 108 can comprise a screen (e.g., an LCD screen) as well as one or more audio speakers—the screen can be associated with a video driver and the one or more audio speakers can be associated with a sound driver. Similarly, the network interface, the sensor interface, the therapy delivery interface, the bus 118, and the communication circuit 120 can each be associated with separate drivers. Device drivers can be software instructions or programs that act as a translator between a hardware device and the applications or operating systems that use it, such as by providing a set of routines that can be called by calling programs operating on the operating system being implemented by processor 122. When a calling program invokes a routine in the driver, the driver can issue commands to the device. Drivers can be hardware-dependent and operating-system specific, and can provide interrupt handling for any necessary asynchronous time-dependent hardware interface.

Drivers can be stored in a driver storage section 126 of non-volatile data storage 104. At startup, the medical device controller 100 can load needed drivers from driver storage section 126 into volatile memory 116. From there, the drivers can be called and invoked by processor 122 in order to control peripheral devices, such as location manager 114, sensor interface 112, bus 118, communication circuit 120, network interface 106, user interface 108, and therapy delivery interface 102. While drivers can simplify and/or facilitate the processor 122's operation and control of associated peripherals, they are not always necessary for the processor to control or use peripherals. In some embodiments, the processor 122 can exercise limited control of at least some features of its connected peripherals even when the associated drivers have not yet been loaded into volatile memory 116.

The medical device controller 100 has a variety of potential applications and is well suited to devices that notify external entities of a variety of events, some of which may require a predetermined response from the external entity. Predetermined responses can include any response that is appropriate given the event being reported. Predetermined responses can include acknowledgment of the alarm, entry of information indicating that the alarm is being addressed and rectification of the event or condition that triggered the alarm. Examples of devices to which the medical device controller 100 is well suited include critical care medical devices, such as a wearable ambulatory external defibrillator, an Automated External Defibrillator (AED), or a mechanical chest compression device, such as the Autopulse® system from ZOLL Medical Corporation of Chelmsford, Mass.

Figure 2:
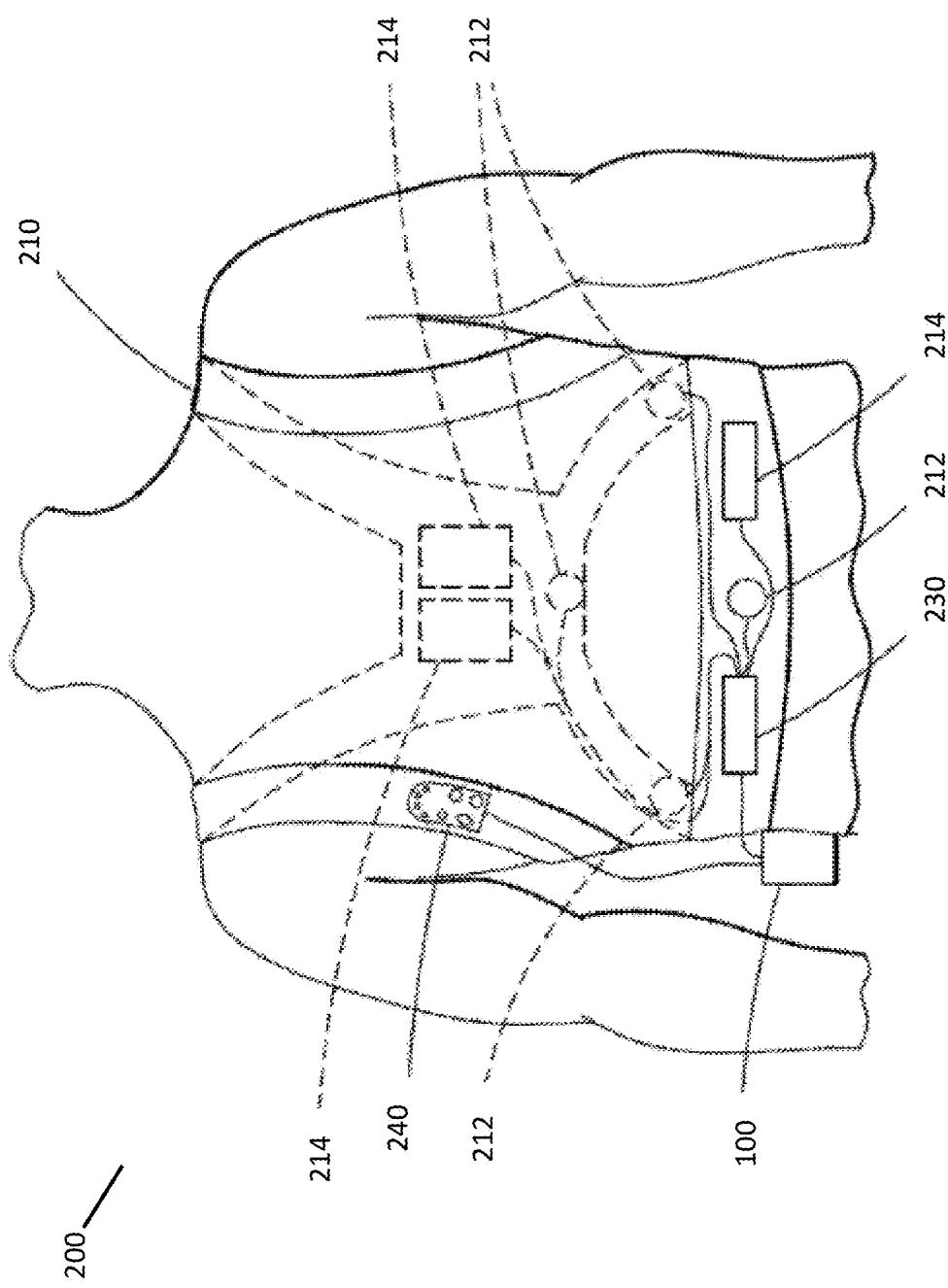
FIG. 2 illustrates a wearable defibrillator, according to some embodiments.

In one embodiment, the medical device is a wearable defibrillator that includes a garment (e.g., a vest or belt) that is worn by the patient. The wearable defibrillator monitors the patient's ECG with sensing electrodes, detects life threatening arrhythmias, and delivers a cardioverting or defibrillating shock through the therapy pads if treatment is necessary. FIG. 2 illustrates a wearable defibrillator, such as a LifeVest® wearable cardioverter defibrillator available from ZOLL Medical Corporation of Chelmsford, Mass. As shown, the wearable defibrillator 200 includes a harness 210 having a pair of shoulder straps and a belt that is worn about the torso of a patient. The wearable defibrillator 200 includes a plurality of ECG sensing electrodes 212 that are attached to the harness 210 at various positions about the patient's body and electrically coupled to the sensor interface 112 of the medical device controller 100 via a connection pod 230. The plurality of ECG sensing electrodes 212, which may be dry-sensing capacitance electrodes, are coupled to the medical device controller 100 to monitor the cardiac function of the patient and generally include a front/back pair of ECG sensing electrodes and a side/side pair of ECG sensing electrodes. Additional ECG sensing electrodes may be provided, and the plurality of ECG sensing electrodes 212 may be provided at varying locations about the patient's body.

The wearable defibrillator 200 also includes a plurality of therapy electrodes 214 that are electrically coupled to the medical device controller 100 via the connection pod 230 and which are configured to deliver one or more therapeutic defibrillating shocks to the body of the patient, if it is determined that such treatment is warranted. The connection pod 230 electrically couples the plurality of ECG sensing electrodes 212 and the plurality of therapy electrodes 214 to the therapy delivery interface 102 and/or the sensor interface 112 of the medical device controller 100, and may include electronic circuitry. The connection pod 230 may also include other electronic circuitry, such as a motion sensor or accelerometer through which patient activity may be monitored.

As shown in FIG. 2, the wearable defibrillator 200 also includes a user interface pod 240 that is electrically coupled to, or integrated in with, the user interface 108 of the medical device controller 100. The user interface pod 240 can be attached to the patient's clothing or to the harness 210, for example, via a clip (not shown) that is attached to a portion of the interface pod 240. Alternatively, the user interface pod 240 may simply be held in a person's hand. In some embodiments, the user interface pod 240 may communicate wirelessly with the network interface 106 and/or user interface 108 of the medical device controller 100, for example, using a Bluetooth®, Wireless USB, ZigBee, Wireless Ethernet, GSM, or other type of communication interface.

The user interface pod 240 includes a number of buttons by which the patient, or a bystander can communicate with the medical device controller 100, and a speaker by which the medical device controller 100 may communicate with the patient or the bystander. For example, where the medical device controller 100 determines that the patient is experiencing cardiac arrhythmia, the medical device controller 100 may issue an audible alarm via a speaker on the medical device controller 100 or the user interface pod 240 alerting the patient and any bystanders to the patient's medical condition. The medical device controller 100 may also instruct the patient to press and hold one or more buttons on the user interface 108 of the medical device controller 100 or on the user interface pod 240 to indicate that the patient is conscious, thereby instructing the medical device controller 100 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient.

In embodiments where medical device controller 100 is implemented within or in conjunction with a wearable defibrillator, the rapid startup and pre-flight methods, systems, and apparatus described herein may be used to display a startup screen, such as a logo, upon power-up. In some embodiments, the medical device controller 100 may utilize the rapid startup and pre-flight methods, systems and apparatus described herein to conduct tests while the device is booting up. These methods, systems, and apparatus are described in further detail below.

Figure 3B:
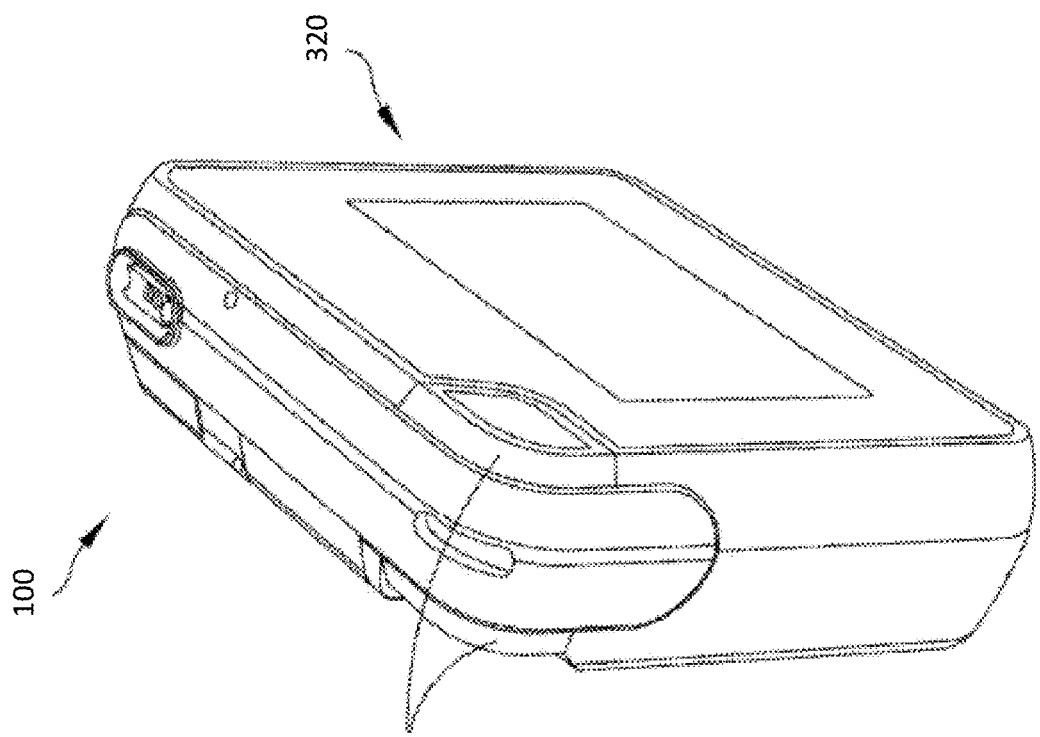
FIG. 3A and FIG. 3B illustrate an exemplary emergency medical device, according to some embodiments.
Figure 3A:
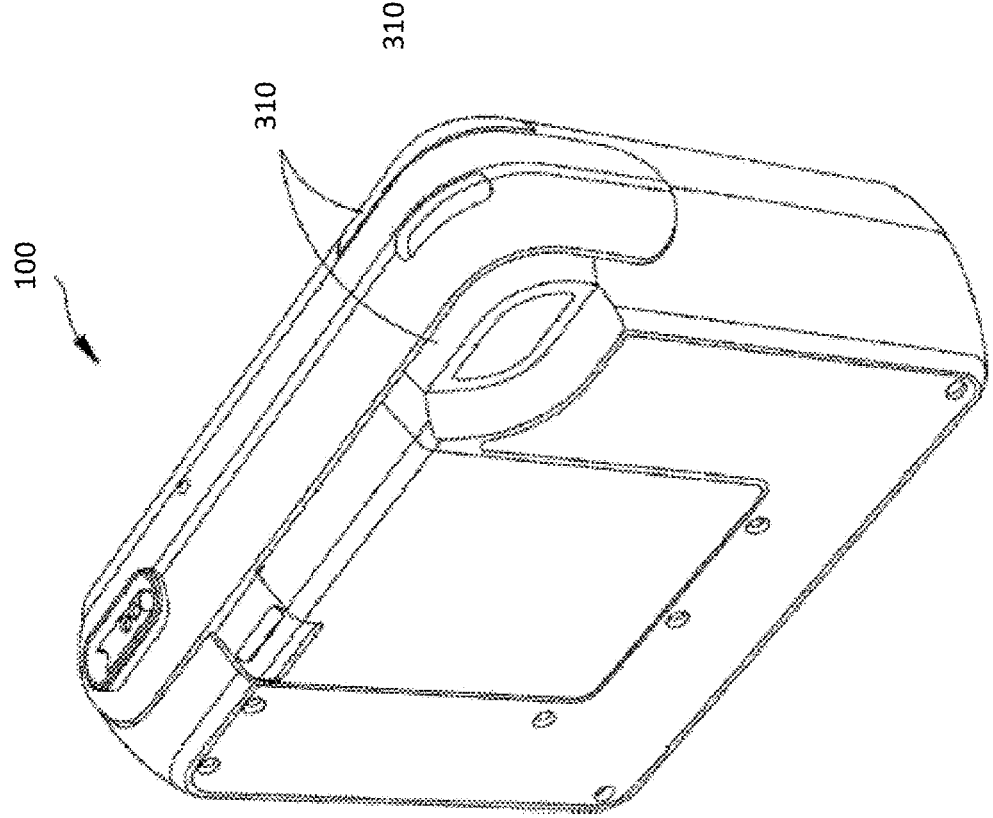

In another embodiment, the functionality of the user interface pod 240 is integrated into the housing of the ambulatory medical device controller 100. FIGS. 3A-B illustrates such an example of the ambulatory medical device controller 100. The ambulatory medical device controller 100 includes two response buttons 310 on opposing sides of the housing of the ambulatory medical device controller 100. As shown in FIGS. 3A-B, the response buttons 310 are recessed to reduce the likelihood of accidental activation (e.g., a patient falling on the response button). The ambulatory medical device controller 100 also includes, in this embodiment, a display screen 320 and a speaker to enable the communication of audible and visual stimuli to the patient. It is appreciated that the response buttons 310 do not have to be placed on opposing sides of the housing as illustrated in FIGS. 3A-B. The response buttons, for example, may be located adjacent to each other in the housing the ambulatory medical device controller. The adjacent placement of the response buttons may make it easier for individuals with smaller hands or less dexterity to engage the response buttons.

Figure 4:
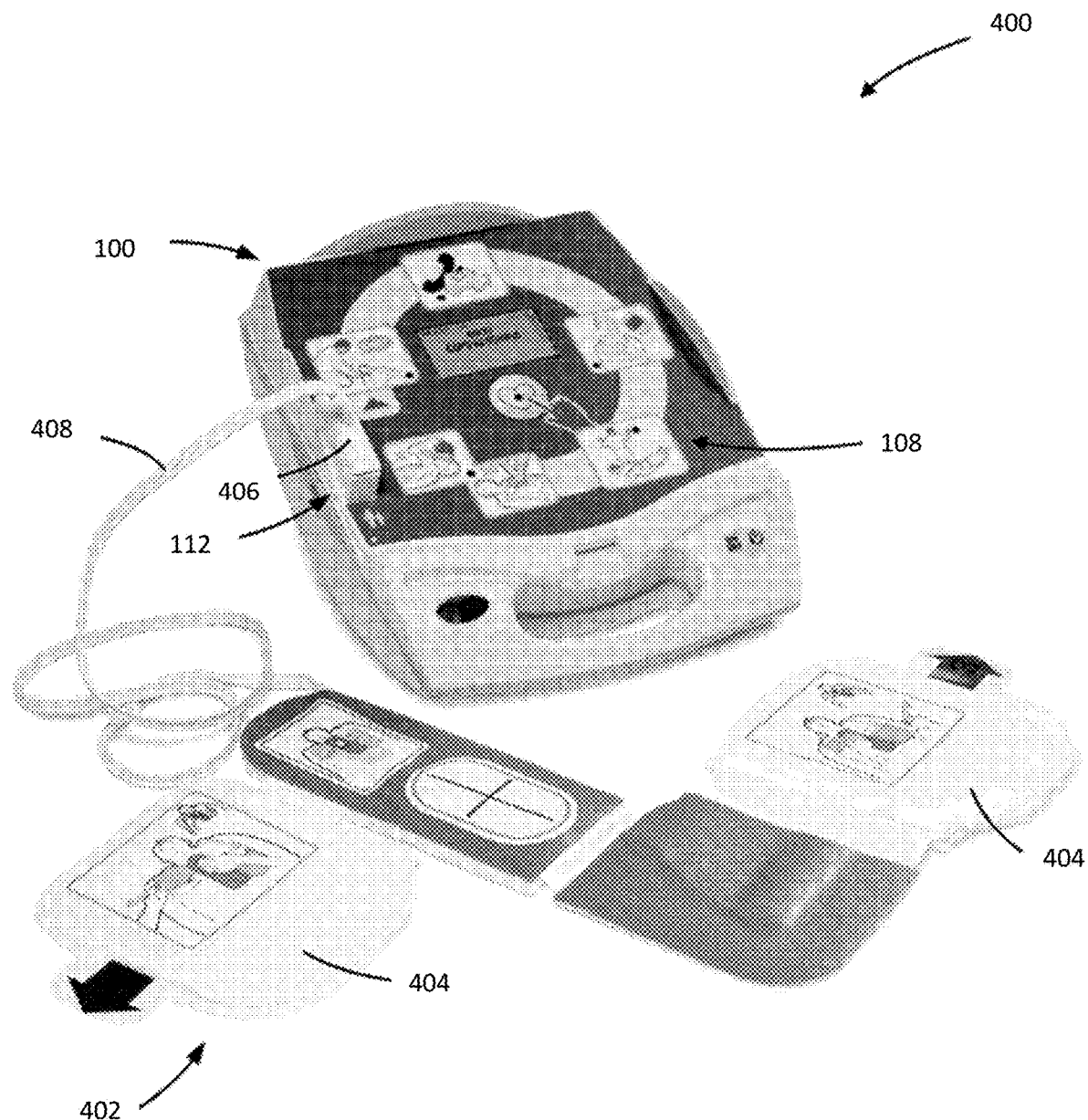
FIG. 4 illustrates an automated external defibrillator, according to some embodiments.

Another example of a medical device is the ambulatory external defibrillator described in FIG. 3 of the '096 application. In at least one embodiment, the ambulatory defibrillator 300 illustrated in FIG. 3 of the '096 application may employ the medical device controller 200, as disclosed in the present application, as a substitute for the portable treatment controller 200 described in the '096 application. In such an embodiment, the ECG Electrodes and Therapy Pads illustrated in FIG. 3 of the '096 application may be logically and physically coupled to the medical device controller 200 via the sensor interface 112 and the therapy delivery interface 102, respectively. While some of the embodiments disclosed herein are directed to medical device controllers in wearable ambulatory medical devices, the medical device controller 200 is well suited for other medical devices including other types of AEDs In one embodiment, the medical device is an AED. AEDs are small portable defibrillators that are capable of monitoring cardiac rhythms, determining when a defibrillating shock is necessary, and administering the defibrillating shock either automatically, or under the control of a trained rescuer (e.g., an EMT or other medically trained personnel). The AED, in addition, may be configured to provide counseling to an operator as to how to perform cardiopulmonary resuscitation (CPR). FIG. 4 illustrates an AED, such as an automated external defibrillator available from ZOLL Medical Corporation of Chelmsford, Mass. As shown, the AED 400 includes a medical device controller 100 and an electrode assembly 402.

The electrode assembly 402 includes one or more sensing electrodes 404 (e.g., ECG sensors), one or more therapy electrodes 404 (e.g., defibrillation pads), a connector 406, wiring 408 electrically coupling the connector 406 to the one or more sensing electrodes 404 and one or more therapy electrodes 404. As shown in FIG. 4, the connector is configured to couple the electrode assembly 402 to the medical device controller 100 and, more specifically, the one or more sensing electrodes to the sensor interface 112 and the one or more therapy electrodes to the therapy delivery interface.

The medical device controller 100 of the AED 400 is configured to detect the cardiac rhythm of the patient and provide defibrillating shocks to the patient as appropriate. This process is similar to the process described with regard to medical device controller 100 of the ambulatory medical device 200. The user interface 108 of the AED 400 may include a variety of components configured to communicate with the operator including, but not limited to, a display screen, a speaker, and one or more buttons. In this embodiment, the AED 400 includes a display screen to display notifications to an operator. The notifications may provide instructions to the operator regarding the proper administration of CPR to the patient. The notifications on the display may be accompanied by audible alerts from the speaker to further assist the operator in administering CPR to the patient.

Figure 5:
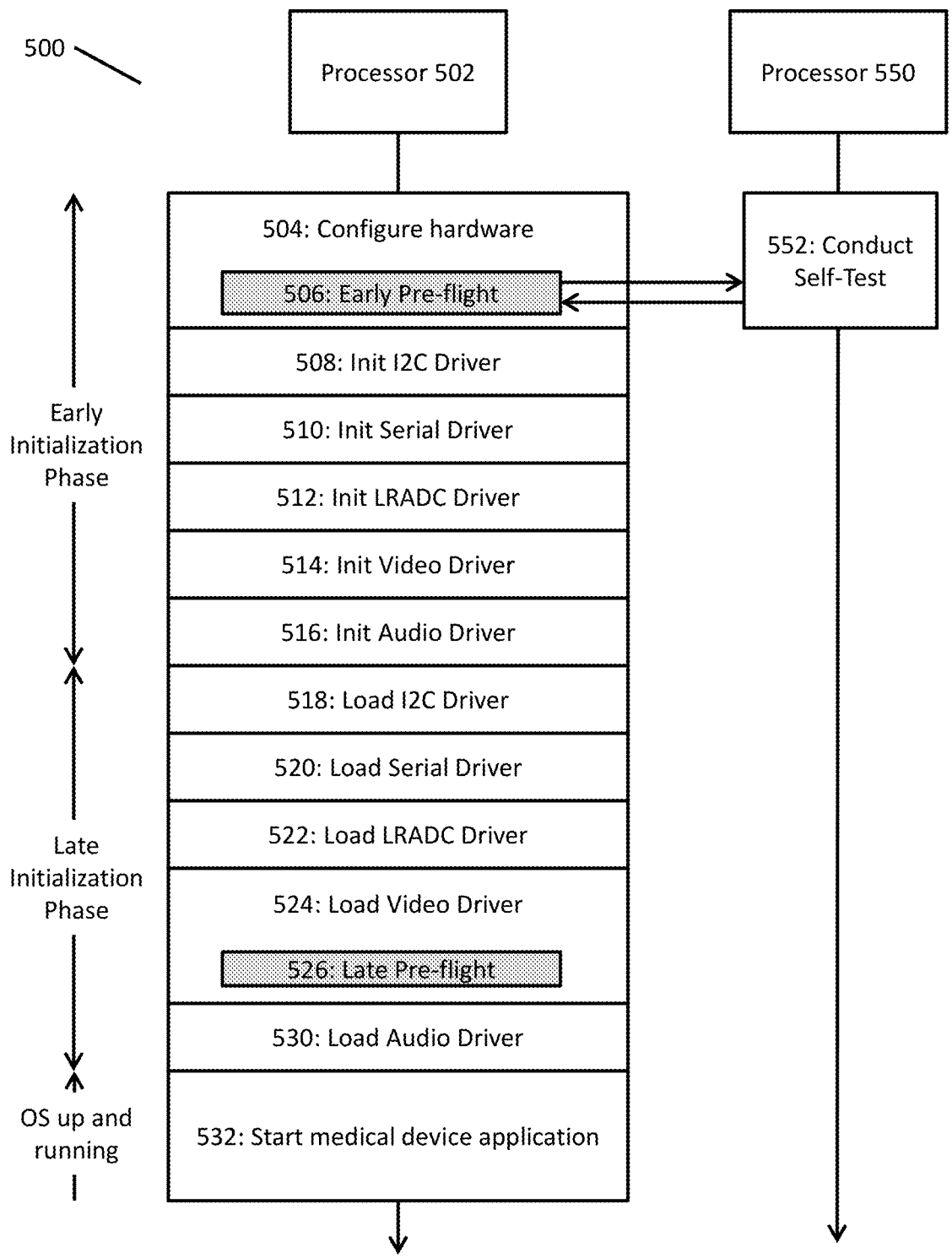
FIG. 5 illustrates an exemplary boot process that can be used to conduct early tests on the functionality of various operational circuits, according to some embodiments.

FIG. 5 illustrates an exemplary boot process 500 that can be used to conduct early tests on the functionality of various operational circuits. In some embodiments, boot process 500 can facilitate conducting such tests earlier in a boot process than other known systems, as well as facilitate reporting on the results of such tests earlier in a boot process than other known systems. As provided herein, operational circuits may refer to any suitable hardware component used to implement one or more functionalities of a medical device. Examples of operational circuits can include both general-purpose circuits (e.g., general-purpose or programmable processors or microprocessors, general-purpose memory) or circuits specially configured or adapted for a specific purpose. Further examples of operational circuits can include without limitation any of the sensing devices, therapy delivery devices, user interface devices, memory storage and retrieval devices, battery or power devices, data buses, internal communication circuits (e.g., UART or analog-to-digital converters), and/or network communication devices, as described above. In the exemplary embodiment described in FIG. 5, process 500 includes a series of stages executed in sequential order from top to bottom. Also, for purposes of illustration, process 500 is shown as being implemented on two processors, a first processor 502 implementing, for example, a general-purpose operating system or GPOS, and a second processor 550 implementing, for example, a real-time operating system or RTOS. However, the present disclosure is not so limited and can be extended to systems utilizing only a single processor (e.g., running multiple process), or more than two processors.

By way of general overview, boot process 500 can be divided into at least two phases in some embodiments, labeled "early initialization phase" and "late initialization phase". During the "early initialization phase", various drivers associated with peripherals in the medical device may not yet have been loaded, virtual addressing may not have been created yet, and operating system code can have full access to processor 502's hardware register(s). In some embodiments, the "early initialization phase" may also correspond to a time when a kernel of the operating system operating on processor 502 runs as a single-threaded entity. Code executed by the processor 502 during the early initialization phase may correspond to code that is part of the operating system kernel, part of the board-support code, or even part of the boot loader code. During this phase, some or all drivers can be run through their initialization (e.g., init ( )) stages, which is a time when the kernel is gathering information on the system capabilities. For example, the kernel can gather information regarding what hardware is available and determine what software or drivers need to be loaded.

Once early initialization is complete, the boot process 500 may enter the late initialization phase. During this phase, boot process 500 can begin loading drivers (e.g., via probe ( ) calls). In some, but not all embodiments, the late initialization phase also corresponds to a part of the boot process 500 where the processor switches from a single-threaded entity to a multi-threaded entity, e.g., the processor begins executing multiple process threads simultaneously. When drivers are fully loaded, boot process 500 can be considered to be complete and the operating system on processor 502 can be considered to be up and running. The operating system can then start running application software, such as a medical device application software. While FIG. 5 illustrates an embodiment of the overall boot process, it can be appreciated that the boot process may be configured to load software components in any suitable manner. For example, drivers may be initiated by separate processors or processor cores, apart from or in connection with self-test protocols.

In some implementations, at least some of the drivers for peripherals coupled to the processor can be associated with corresponding processor registers. For example, a driver for the communication circuit 120 can have a corresponding communication circuit processor register, a driver for the user interface 108 can have a corresponding user interface processor register, etc. Before or while drivers are being run through their initialization (e.g., init( )) stages, and before the drivers are fully loaded and operating, operating system code can have direct read/write access to processor registers corresponding to each of the drivers. Operating system code can be distinct from driver code in that they can comprise instructions that are part of an operating system's kernel or bootloader. Operating system code can also be distinct from application code that implements applications that run on the operating system. However, once a driver's probe function is called and the driver is loaded and operating, the driver can take over control over its corresponding processor register. In some instances, when this happens, the operating system stops accessing the driver's registers directly, and instead interacts with the registers only via the loaded driver's call functions. This is because if the operating system continues to directly access the driver's registers without going through the driver, the operating system can, in some instances, introduce errors into the driver's operations, as the operating system may make changes in the driver's registers without the driver's knowledge. For example, when the drivers corresponding to the communication circuit 120 is loaded (such as a UART driver), operating system code can no longer access the processor register corresponding to communication circuit 120.

As provided in an illustrative embodiment, the boot process 500 may begin by executing stage 504 at processor 502. Stage 504 can be the first stage that is executed at processor 502 after the medical device is activated or powered on, and can comprise configuration of hardware within processor 502 and/or within peripherals connected to processor 502. This stage can comprise various basic system integrity checks, loading of the basic input/output system (BIOS), loading and execution of a bootloader, loading and execution of a Master Boot Record, and/or loading and execution of a Grand Unified Bootloader (GRUB).

The Configure Hardware stage 504 can also comprise an "Early Pre-Flight" sub-stage 506. At a high level, Early Pre-Flight sub-stage 506 can be a set of operations implemented by operating system code stored in Pre-Flight Data Store 124, in non-volatile data storage 104. In some embodiments, such a stage may be provided as part of an early-testing process that informs a user that the device is able to function according to suitable specifications, or at least provide the user with comfort and/or knowledge that basic functionalities (e.g., self-test, shock button readiness, user interface, or other features) of the device are operational. This stage may also provide the user with other indications, such as instructions for administering resuscitative action (e.g., provide CPR, call for help and/or emergency services, etc.) and/or indicate the progress of initialization of other components (e.g., battery test, driver initialization, amongst others). Early Pre-Flight sub-stage 506 can be called as part of the Configure Hardware stage 504, or immediately after Configure Hardware stage 504. In Linux-based implementations, for example, Early Pre-Flight sub-stage 506 can be called between the functions mx28_ccardxmx28_pins_init( ) and mx28_device_init( ) located in the function mx28_ccardxmx28_init_machine( ). Early Pre-Flight sub-stage 506 can initiate and/or report on various tests on operational circuits, and access and configure needed hardware resources in order to conduct said tests. Notably, the tests initiated at the Early Pre-flight sub-stage 506 can be implemented on certain operational circuits even before the drivers for those modules are loaded. This can be done by using operating system code to operate said operational circuits before the associated drivers have been loaded.

In slightly more detail, Early Pre-Flight sub-stage 506 can configure bus 118 (e.g., an I2C bus) for operation, read hardware revision information (e.g., from a General Purpose Input/Output (GPIO) pin), configure user interface 108 by configuring speaker hardware and/or display hardware for operation by operating system code (e.g., by configuring codecs and amplifiers for audio/display use), and communicate with processor 550 through bus 118 to initiate and/or fetch Power-On Self-Test (POST) information. The initiation and/or fetching of POST information is illustrated in FIG. 5 as a bi-directional arrow between sub-stage 506 and Conduct Self-Test stage 552 being executed on Processor 550. While FIG. 5 depicts a bi-directional arrow however, it is appreciated that communication between Processors 502 and Processor 550 can be uni-directional in some embodiments.

Figure 6:
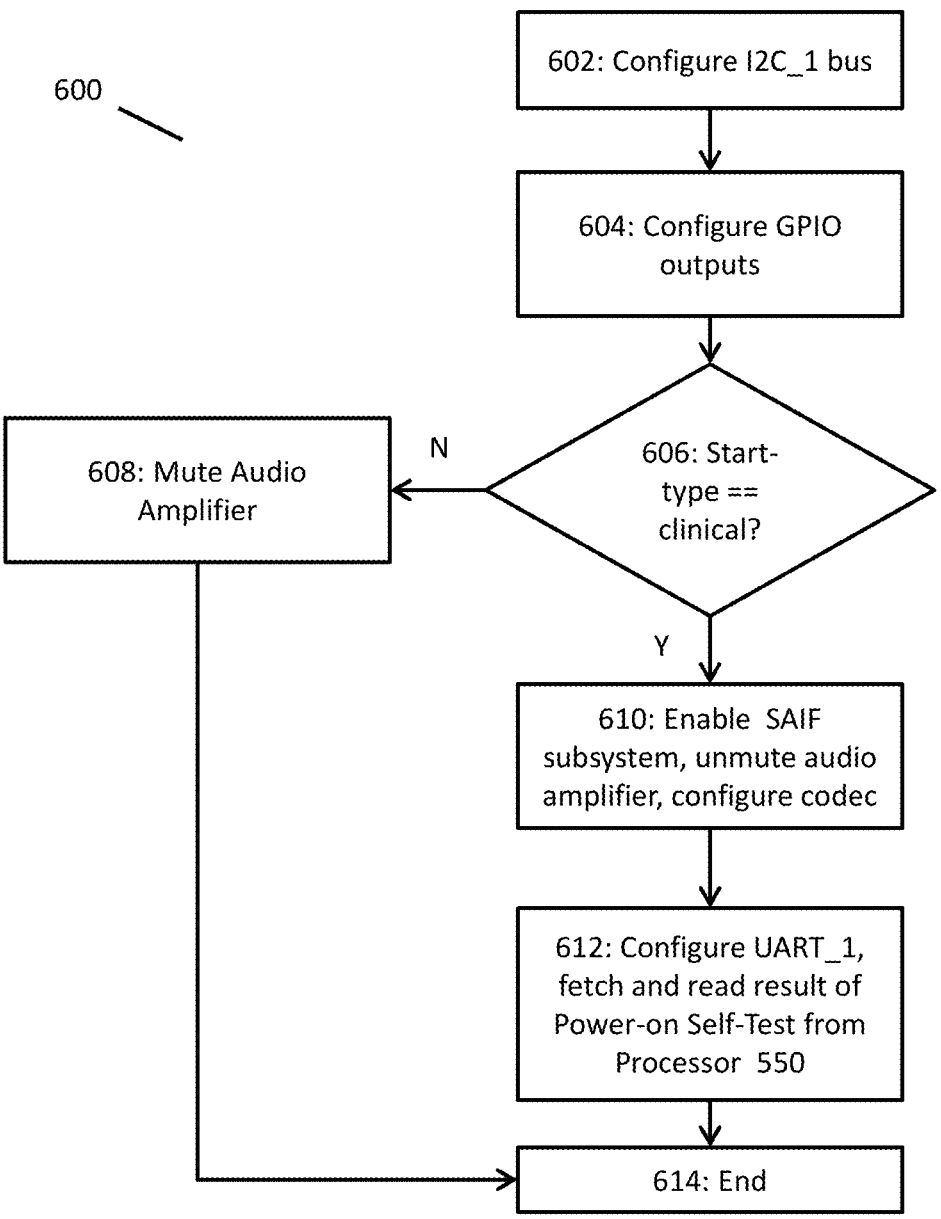
FIG. 6 is a flow-chart illustrating an exemplary process that can be implemented as part of an Early Pre-Flight sub-stage, according to some embodiments.

FIG. 6 is a flow-chart illustrating an exemplary process 600 that can be implemented as part of Early Pre-Flight Sub-stage 506. At stage 602, bus 118, such as I2C_1 bus, can be configured for operation. This can comprise the operating system detecting a hardware type or revision of bus 118, and configuring bus 118 to enable operating system code to access a GPIO expander for reading/setting various I/O pins (e.g., audio mute) and to access an audio codec in order to play audio prompts. Notably, since the driver for bus 118 has not yet been loaded, and operating system code still retains full access to all processor registers at this point in the boot process 500, the operating system can directly access and use bus 118 even without the aid of a driver.

At stage 604, process 600 can configure GPIO outputs for audio/display use. This can comprise executing code that assigns certain GPIO pins for use in transmitting or relaying audio or display data.

At stage 606, process 600 can determine whether the medical device is being started in a clinical mode or a non-clinical mode. In some embodiments, clinical mode can correspond to a mode in which the medical device is being used to treat, monitor, or otherwise aid a patient in a medical situation. Non-clinical mode can be a mode in which the medical device is being turned on for other situations, such as repair and servicing, configuration of settings, and/or updating of software or hardware components. Various ways of entering clinical mode vs. non-clinical mode are possible. For example, non-clinical mode can be entered if the power-on button of the medical device is pressed and held down for 5 or more seconds, and clinical mode can be entered if the power-on button is pressed and held down for less than 5 seconds. If Pre-Flight Sub-stage 506 determines that the medical device has been turned on in clinical mode, Pre-Flight Sub-stage 506 can branch to stage 610. If Pre-Flight Sub-stage 506 determines that the medical device has been turned on in non-clinical mode, in some cases, Pre-Flight Sub-stage 506 can branch to stage 608.

At stage 610, process 600 can configure speaker hardware associated with the medical device for operation. This can comprise enabling a Serial Audio Interface (SAIF) subsystem or other audio subsystem, configuring clocks on the SAIF/audio subsystem to allow access via bus 118, unmuting an audio amplifier, and configuring a codec to allow operating system code to directly output sound via speaker hardware.

At stage 612, process 600 can configure communication circuit 120 (e.g., a UART) to fetch and read results of a Power-on Self-Test from Processor 550. In some embodiments, Processor 502 can instruct Processor 550 to conduct a Power-on Self-Test, and then retrieve the results via communication circuit 120 and/or bus 118. In some embodiments, Processor 550 can automatically implement a Power-on Self-Test without any prompting from Processor 502 when the power for the medical device is activated, and then relay the results of the Self-Test via communication circuit 120 and/or bus 118. In some embodiments, Processor 550 can implement a Defibrillator Engine software module that operates a defibrillator shock device. During a Power-on Self-Test, processor 550 can test various aspects of the defibrillator shock device, such as whether a safe line is operating properly in both an off state and an on state, whether a defibrillator capacitor can charge properly (e.g., charge to at least 2 joules), whether a patient relay driver can be switched between an on/off state, whether bridge control arms can be switched to an on/off state, whether one or more watchdog timers for processor 550 is operating properly, whether one or more system timers for processor 550 is operating properly, whether memory associated with processor 550 is operating properly, whether an analog-to-digital converter (ADC) is operating properly, whether a shock button that triggers a therapeutic electric shock (e.g., a defibrillator or pacing electric shock) is operating properly (e.g., whether the shock button is stuck) and/or whether a battery voltage is above a pre-determined threshold (e.g., 8.0 volts). In some implementations, processor 550 can be configured to complete the Power-on Self-Test within four seconds after the medical device is powered on, Processor 550 can also be configured to transition to an idle mode after completion of the Power-on Self-Test, and can send processor 502 the results of the Self-Test. If a critical fault occurs, processor 550 can be configured to disable the defibrillator functionality of the medical device. If no faults are detected, or if only non-critical faults are detected, processor 550 can enable the defibrillator functionality of the medical device.

As provided in FIG. 6, for this illustrative embodiment, if the medical device is started in non-clinical mode, process 600 can branch to stage 608. In some embodiments, the medical device can remain silent (e.g., not enunciate any audible prompts) in non-clinical mode, and as a result there is no need to enable any of the audio subsystems. Therefore, Early Pre-Flight sub-stage 506 can mute the audio amplifier to avoid any "noise" on the speaker.

Process 600 can end at stage 614, thus allowing boot process 500 to continue onto the next stage. In some embodiments, process 600 can also report the results of tests conducted in the Early Pre-Flight sub-stage 506 using an audio tone, a visual display, such as an image or displayed text pre-loaded into memory, a status light, or haptic/vibration feedback to a user at stage 614. Any critical faults detected as part of Early Pre-Flight sub-stage 506 can cause the medical device to display no feedback or different feedback than if no critical faults were detected. Once Early Pre-Flight sub-stage 506 and/or process 600 is finished, the results of the Power-on Self-Test from Processor 550 can be known, the audio codec can be either disabled or enabled (depending on whether the medical device was started in clinical or non-clinical mode), hardware revision information of the medical device will be known, and/or the GPIO can be configured for the booting stage. Late Pre-Flight sub-stage 526, described in more detail below, can require access to the hardware revision and the results of the Power-on Self-Test.

Returning to FIG. 5, for various embodiments, the boot process 500 can continue with stages 508, 510, 512, 514, and 516. In these stages, boot process 500 can implement the init( ) stages of a bus driver (e.g., I2C driver) (stage 508), a communication circuit driver (e.g., a UART or other serial driver) (stage 510), a driver for an analog-to-digital converter (e.g., a Low Rate Analog-to-Digital Converter (LRADC) driver or other ADC) (stage 512), a video driver (e.g., a LCDIF driver) (stage 514), and an audio driver (e.g., a driver for the SAIF subsystem) (stage 516). As described above, the init( )stage of a driver can be a time where the operating system kernel on processor 502 gathers information on system capabilities, such as what hardware is available and what software needs to be loaded. At this point, boot process 500 continues to operate as a single-threaded entity.

It is to be appreciated that any or all of the tests described above as being executed by processor 550 during the Power-on Self-Test may also be performed by processor 502 as part of, or in-between, stages 508, 510, 512, 514, and/or 516. For example, the test to see whether the shock button is stuck or not may be performed as part of stage 512, in which the ADC driver (e.g., LRADC driver) is initiated, or may be performed before or after stage 512.

For the example provided, by the beginning of stage 518, all drivers have completed their init( ) stages and the operating system on processor 502 begins loading drivers. The loading of various drivers can, in some embodiments, mark the end of the early initialization phase and the beginning of the late initialization phase. Specifically, boot process 500 can load the bus driver (e.g., I2C driver), communication circuit driver (e.g., UART or other serial driver), analog-to-digital converter driver (e.g., ADC driver, LRADC driver), video driver (e.g., LCDIF driver), and audio driver (e.g., driver for SAIF subsystem) at stages 518, 520, 522, 524, and 530, respectively. In some but not all embodiments, starting with stage 518, the processor 502 can begin utilizing multiple simultaneous process threads. Loading of drivers can be implemented via probe( ) calls. As discussed above, once a driver's probe function is loaded, the driver can have control over the processor register that it owns. In some embodiments, operating system code can no longer access a driver's registers once the driver is fully loaded.

The Load Video Driver stage 524 can also comprise a "Late Pre-Flight" sub-stage 526. At a high level, late pre-flight sub-stage 526 can also be a set of operations implemented by operating system code stored in Pre-Flight Data Store 124, in non-volatile data storage 104. Late Pre-Flight sub-stage 526 can be called as part of the Load Video Driver stage 524, as a separate process thread that is executed at the same time as Load Video Driver stage 524, or immediately before or after Load Video Driver stage 524. Late Pre-Flight sub-stage 526 can also be called earlier or later in the late initialization phase, such as before or during stage 518, 520, or 522, or during or after stage 530. In some preferred embodiments, Late Pre-Flight sub-stage 526 is executed before audio drivers are loaded in stage 530, which ensures that operating system code can access the sound subsystem during the Pre-Flight sub-stage 526. Late Pre-Flight sub-stage 526 can load at least some of the contents of Pre-flight Data Store 124 into a section of volatile memory 116, remap that section of volatile memory into a kernel-accessible region, verify the integrity of Pre-Flight data in the remapped section of volatile memory 116, create and display an initial startup image, which can comprise a logo as well as an indication of the results of tests conducted during the Early Pre-Flight stage 506, and/or enunciate an initial audio prompt. The operation of Late Pre-Flight stage 526 can differ depending on whether the medical device was started in clinical mode or non-clinical mode.

FIG. 7 is a logical block diagram illustrating at least part of the contents 700 of Pre-Flight Data Store 124 that is copied into volatile memory and remapped into a kernel-accessible region (e.g., so that the contents 700 can be presented to the operator, such as after completion of the Early Pre-flight sub-stage 506). Contents 700 can comprise a header 702, which can be a record (e.g., database) indicating the contents of the Pre-Flight Data Store 124 and instructions regarding how to access said contents. For example, the header can contain a list of the various audio/video items stored in Pre-Flight Data Store 124, their memory locations (e.g., memory offsets), and their length. Header 702 may also store device-specific information, such as hardware and/or software revision, device type, whether the device is a fully automatic unit or semi-automatic unit, etc. These configuration details may affect how the self-test results are used.

Contents 700 can also comprise a "Call for Help" block image 704, which can be an image of the words "Call for Help," or other suitable graphic. Contents 700 can also comprise a "Unit Failed" ribbon image 706, a "Unit OK" ribbon image 708, and a "Battery Test in Progress" ribbon image 710, which can be an image of the words "Unit Failed", "Unit OK", and "Battery Test in Progress", respectively. Contents 700 can also comprise a "Unit Failed" audio prompt 712 and a "Unit OK" audio prompt 714, which can be sound data encoded in a binary format that, when played by a sound subsystem, can enunciate the audible words "Unit Failed" and "Unit OK", respectively. Contents 700 can also comprise a Data Integrity Check 716 that can be used to verify the integrity of contents 700, e.g., to check whether the contents 700 have been corrupted or not. Data Integrity Check 716 can comprise a cyclic redundancy check (CRC), an Adler-32, or a hash of all or part of contents 700. It can be appreciated that any appropriate series of images and/or audio output(s) may be stored in memory and accessed at a suitable time to provide a user with confidence that the device functions as intended. By storing such images and/or audio as part of Pre-Flight Data Store 124 (as opposed to hard-coding such images and/or audio files into operating system code), manufacturers can easily alter such images and/or audio files without having to rewrite operating system code. Maintaining this flexibility to edit images and/or audio can facilitate adapting medical devices to use different languages, adapting the same software structure for use in different types of medical devices, or to incorporate different or updated instructions and tests.

Figure 8:
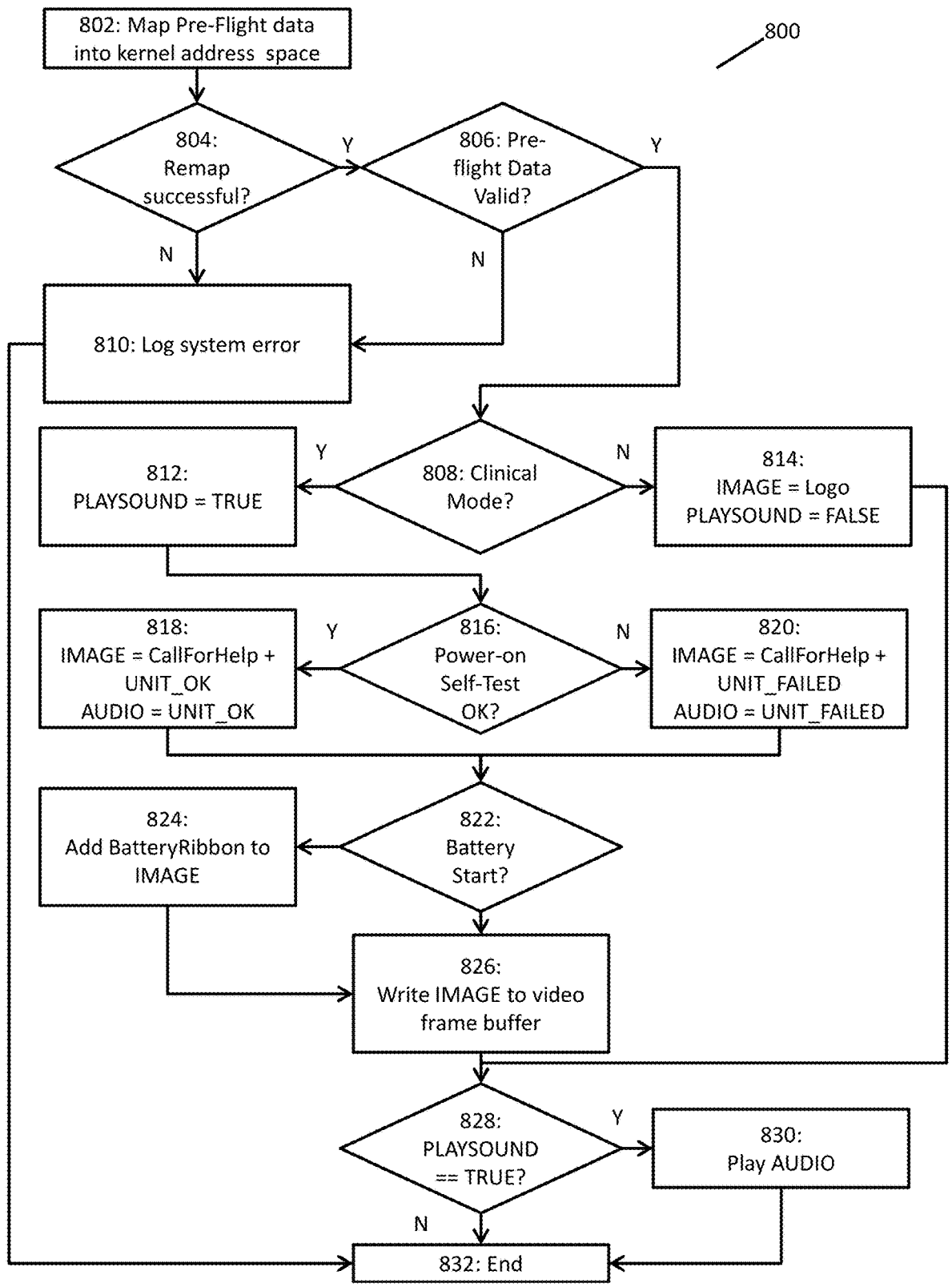
FIG. 8 is a flow-chart illustrating an exemplary process that can be implemented as part of a Late Pre-Flight sub-stage, according to some embodiments.

FIG. 8 is a flow-chart illustrating an exemplary process 800 that can be implemented as part of Late Pre-Flight Sub-stage 526. At stage 802, process 800 can copy contents 700 into a section of volatile memory 116, and remap that section of volatile memory 116 into a kernel-accessible region of memory.

At stage 804, process 800 can verify if the remap was successful. If the remap was not successful, sub-stage 526 can branch to stage 810 where it logs a system error, and then to stage 832 where process 800 can end. If the remap was successful, sub-stage 526 can branch to stage 806.

At stage 806, process 800 can determine if the section 700 of pre-flight data that was copied and remapped is valid. This can comprise verifying the integrity of the data in section 700 using the Data Integrity Check 716. If the pre-flight data is determined to be invalid, the pre-flight data may have been corrupted in storage or during the copying and/or remapping process. In that case, process 800 can branch to stage 810 where it logs a system error, and then to stage 832, where the process ends. If the pre-flight data is determined to be valid, process 800 can branch to stage 808.

At stage 808, process 800 can determine if the medical device was started in clinical mode. If the device was started in clinical mode, process 800 can branch to stage 812, where process 800 can enable audio messages by setting a binary variable PLAYSOUND to TRUE, and then branching to stage 816. If the device was not started in clinical mode, process 800 can branch to stage 814, where process 800 can set an image variable "IMAGE" to be equal to a default logo, such as the logo of a manufacturer or service provider. Stage 814 can also optionally disable audio messages by setting the binary variable PLAYSOUND to FALSE. From stage 814, process 800 can branch to stage 828, described below.

At stage 816, process 800 can determine if the results of the Power-on Self-Test retrieved during Early Pre-Flight sub-stage 506 indicate any critical faults. In some embodiments, any faults that can be detected can be a critical fault; in some embodiments, only some faults that can be detected can be deemed a critical fault. Non-limiting examples of critical faults can include faults that prevent the medical device from delivering a safe or effective therapeutic electric shock or other medical treatment. Non-limiting examples of non-critical faults can include faults in the medical device's user interface or network interface. In some cases, which faults are deemed critical faults and which faults are deemed non-critical faults can depend on the device's configuration, as determined from reading the contents of header 702 of Pre-Flight Data Store 124. For example, if header 702 indicates that the device is configured as an automatic defibrillator, a malfunctioning shock button can be a non-critical fault, since the device will automatically shock the patient when it determines such a shock is necessary (e.g., without user input). On the other hand, if header 702 indicates that the device is configured as a non-automatic or manual defibrillator, a malfunctioning shock button can be a critical fault, as a user would then have no way of initiating a defibrillator shock. While FIG. 8 describes the checking of results of the Power-on Self-Test, it is to be appreciated that the results of any previously conducted tests may also be checked during stage 816, whether these tests were conducted as part of the Power-on Self-Test, or were conducted independently as part of other processes.

If critical faults were not detected, process 800 can branch to stage 818, where process 800 can set image variable "IMAGE" to include the "Call for Help" block image 704 and the "Unit OK" ribbon image 708, and set an audio variable "AUDIO" to be equal to the "Unit OK" audio prompt 714. If critical faults were detected, process 800 can branch to stage 820, where process 800 can set the image variable "IMAGE" to include the "Call for Help" block image 704 and the "Unit Failed" ribbon image 706, and the audio variable "AUDIO" to be equal to the "Unit Failed" audio prompt 712. When complete, both stages 818 and 820 can branch to stage 822.

At stage 822, process 800 can determine if the medical device was started and/or is currently being powered by a battery (as opposed to being plugged into a relatively non-exhaustible power source, such as a wall outlet). If the device is being powered by a battery, process 800 can branch to stage 824, where process 800 can add the contents of "Battery Test in Progress" ribbon image 710 to the image variable "IMAGE." Whether or not the device is being powered by a battery, process 800 can continue on to stage 826.

At stage 826, process 800 can write the contents of image variable IMAGE to a video frame buffer, which causes the contents of image variable IMAGE to be displayed on a display of the medical device.

At stage 828, process 800 can evaluate whether the binary variable PLAYSOUND is set to TRUE. If PLAYSOUND is TRUE, process 800 can branch to stage 830, where process 800 causes the audio subsystem of the medical device to play the contents of audio variable "AUDIO". When complete, stage 830 can branch to stage 832, where process 800 ends. If PLAYSOUND is FALSE, process 800 can branch straight to stage 832, where process 800 ends.

The boot process 500 described above in relation to FIGS. 5-8 can be modified in many ways. In some embodiments, boot process 500 can be configured to run on a single processor instead of two processors (e.g., processor 502 and processor 550). In such embodiments, the steps currently being performed by processor 550 can instead be performed by processor 502; for instance, the Power-on Self-Test currently depicted as being part of stage 552 can be initiated, implemented, and/or concluded as part of Early Pre-Flight sub-stage 506 by processor 502. In some embodiments, some or all of the steps depicted as being performed by processor 502 can be performed by a first processor core, and some or all of the steps depicted as being performed by processor 550 can be performed by a second processor core, wherein the first and second processor core are part of a single, multi-core processor.

The boot process 500 can also be modified to incorporate additional tests of operational circuits. For instance, boot process 500 can be modified to conduct tests on the functionality of one or more physiological sensors, such as body temperature sensors, respiration monitors, electrocardiogram (ECG) sensing electrodes, blood oxygen sensors, end-tidal $CO_2$ sensors, pulse oximetry sensors, heartbeat sensors, and blood-pressure sensors and/or one or more environmental sensors such as atmospheric thermometers, airflow sensors, video sensors, audio sensors, accelerometers, GPS locators, and hygrometers. Boot process 500 can also be modified to conduct tests on other types of therapy delivery devices, such as pacing electrodes, mechanical chest compression devices, a respirator, and/or a drug delivery device. Boot process 500 can also be modified to conduct tests on system hardware resources, such as system clocks, watchdog timers, random-access memory (RAM), central-processing units (CPU), and network communication interfaces. Furthermore, instead of or in addition to performing tests on operational circuits, boot process 500 can also be modified to conduct tests on needed software resources, such as necessary language sets, needed libraries/routines, and needed data, picture, video and/or audio files, etc. Boot process 500 can also conduct tests to determine if necessary physical components of the medical device have been properly configured by the user, such as determining whether electrode leads have been properly plugged in, whether plugged in leads are of the appropriate type, determining whether plugged in cables have expired, etc.

In embodiments where the medical device comprises a location manager, boot process 500 can determine if the location manager is functioning properly. Any of the aforementioned tests, as well as other types of tests, can be implemented as part of the Early Pre-Flight sub-stage 506, or as part of the Late Pre-Flight sub-stage 526. If some tests return negative results, the medical device can be configured to report a warning to a user, and/or disable certain functionalities until various critical faults are addressed. Which tests are performed, the order in which the tests are performed, the way in which test results are reported, and determinations regarding what results constitute critical faults vs. non-critical faults can depend on a determined hardware version associated with the medical device.

In some embodiments, instead of having an "Early" Pre-Flight sub-stage 506 and a separate "Late" Pre-Flight sub-stage 526, some or all of the steps described above in relation to sub-stage 506 and sub-stage 526 can be combined into a single Pre-Flight sub-stage. This single pre-flight sub-stage can be implemented at any point during boot process 500, whether in the early initialization phase, or the late initialization phase. The steps described above in relation to sub-stage 506 and 526 can also be re-arranged into more sub-stages, such as three, four, five, or more sub-stages.

In some embodiments, boot process 500 can be modified to report the results of some of the tests described above earlier in the boot process 500, later in the boot process 500, or in different ways than previously described. For example, the medical device can be configured to generate one or more audible tones, and/or activate certain status lights, if certain tests have been passed. The generating of tones and/or activating of status lights can occur before the display "Unit OK" or "Unit Failed" ribbon is displayed as part of process 800 in Late Pre-Flight sub-stage 526, and can indicate that certain operational tests have been passed (e.g., the Power-on Self-Test conducted in stage 552). These indications can indicate more than the simple fact that the device is receiving power—they can instead indicate that certain tests on the functionality of various operational circuits have been implemented and have been successfully passed.

In some embodiments, instead of displaying a ribbon of words indicating "Unit OK" or "Unit Failed", the medical device can instead display a series of check marks next to operational circuits, or display a status wheel indicating which tests have been conducted so far, which tests have been passed, and which tests have resulted in a negative outcome.

The present disclosure is also directed at other techniques for decreasing a perceived boot time associated with the medical device, or otherwise indicating to a user that the medical device falls within suitable operating parameters. In some embodiments, the actual boot times may be decreased. For example, one or more processors associated with the medical device may be run at a first clock speed for an initial time period immediately after the device is turned on, and then one or more processors may be run at a second clock speed after the initial time period has expired. The first clock speed can be higher than the second clock speed, such that running the one or more processors at the first clock speed can facilitate the one or more processors completing all necessary boot steps within a shorter period of time than if the one or more processors had been running at the second clock speed.

The first clock speed can be associated with a first Mean Time Before Failure (MTBF) whereas the second clock speed can be associated with a second MTBF that is longer than the first MTBF. An MTBF associated with a clock speed can be an average time that one or more processors can be expected to operate before failing when operated continuously at that clock speed. Thus, if the one or more processors were to be operated continuously at the first clock speed, the one or more processors could be expected to fail sooner than if the one or more processors were operated continuously at the second clock speed. To diminish the impact on the operational life of the medical device, the one or more processors can therefore be configured to decrease its clock speed to the second, slower clock speed after the initial time period has expired.

Figure 9:
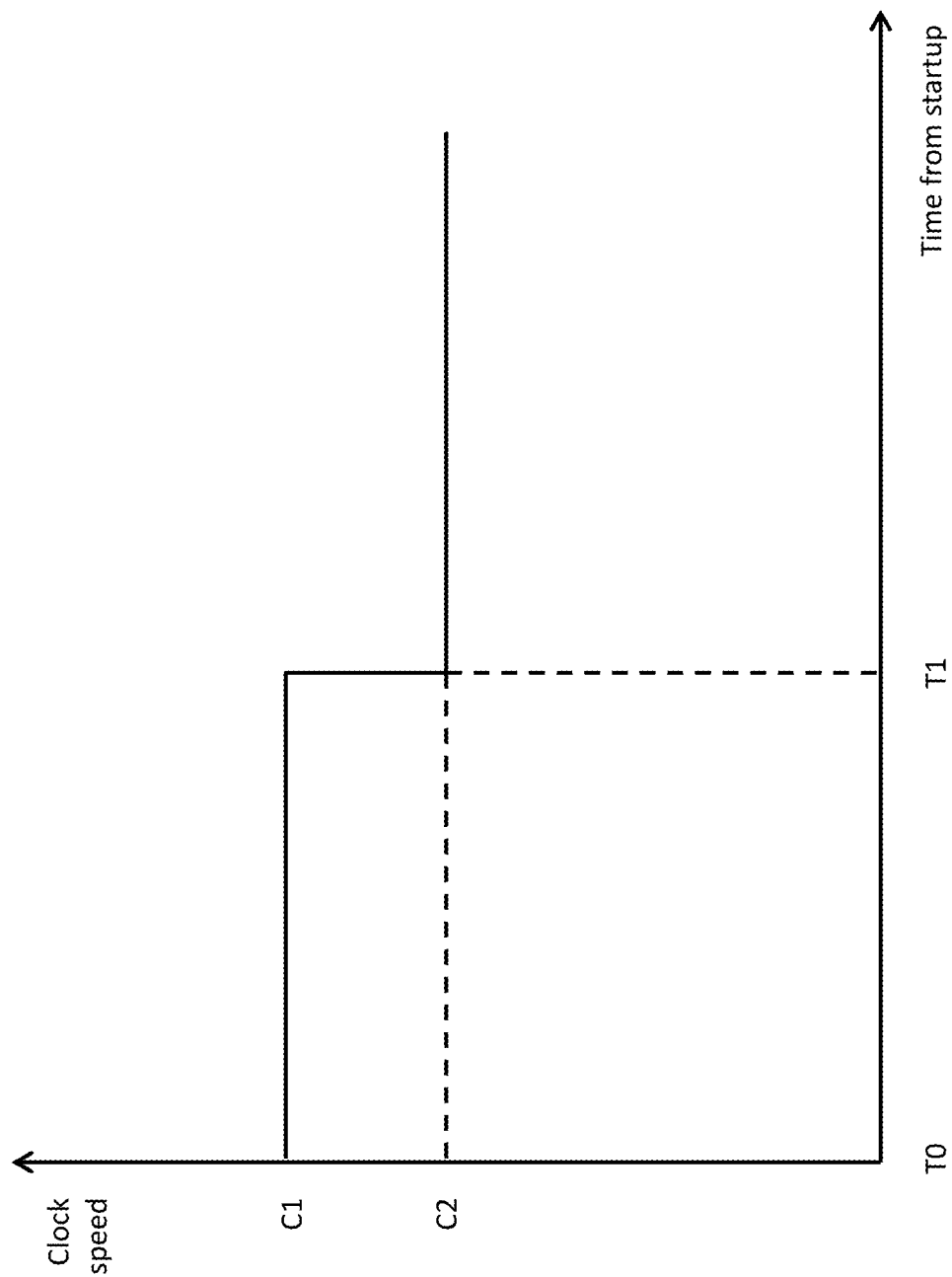
FIG. 9 depicts a plot of clock speed vs. time associated with a medical device, according to some embodiments.

FIG. 9 depicts a plot of clock speed vs. time associated with the medical device, according to some embodiments. The horizontal axis depicts time from startup, wherein t=T0 indicates the time at which the medical device is first activated. The vertical axis depicts a clock speed at which the one or more processors can be run. Between time t=T0 and time t=T1, the one or more processors can be run at clock speed C1, whereas from time T1 onwards, the one or more processors can be run at clock speed C2. C1 can be less than 5% higher than C2, greater than 5% higher than C2, between 5-10% higher than C2, greater than 10% higher than C2, between 10-25% higher than C2, or greater than 25% higher than C2. It should be appreciated that the amount C1 is greater than C2 is not so limited as any suitable range above C2 may be employed.

Operating a processor at a higher clock speed can cause the processor to generate more heat than if the processor were operated at a lower clock speed. If the processor overheats, the processor's operations can become erratic and unreliable, and the processor can be damaged. When the processor first starts up, however, the temperature of the processor and the silicon substrate on which it resides can be expected to be relatively low. As a result, the processor can generally be operated at a faster rate immediately after being powered up than during regular operations. The one or more processors can be configured to operate at the higher clock speed C1 for an initial time period T0 to T1, wherein the initial time period is selected to be short enough such that the processor will generally not overheat before switching to the lower clock speed C2. The processor can thereafter be run at the lower clock speed C2. In some embodiments, the initial time period T0 to T1 can be a variable time period rather than a fixed time period. The one or more processors can also include or otherwise be associated with a temperature sensor, such as an on-chip thermistor that measures the processor temperature. The medical device can be configured to operate the one or more processors at the higher clock speed C1 longer if the thermistor indicates the temperature is relatively low, and to operate at the lower clock speed C2 if the thermistor indicates the temperature is relatively high. For instance, in some embodiments, the medical device can operate the one or more processors at the higher clock speed C1 for as long as the temperature measured by the temperature sensor (e.g., thermistor) is below a certain pre-determined threshold.

Both higher clock speed C1 and lower clock speed C2 can be authorized or approved for safe operation by the processor manufacturer. In some cases, the processor manufacturer can also authorize or approve for safe operation higher clock speed C1 for the initial time period T0 to T1.

Another way to decrease the perceived boot time is to provide the medical device with at least one sensor for sensing one or more parameters of the medical device's surrounding environment. The medical device can infer from the sensed parameters when an activation might be imminent. When the medical device infers that an activation might be imminent, the medical device can preemptively transition from a sleep state (or power off state) to a standby state that begins activation of the medical device without requiring further effort from a user to take proactive steps in turning on the device (e.g., pushing a power button). After entering the standby state, if the medical device then detects that its power, or "ON" button has been actuated, the medical device can quickly transition from the standby state into a fully activated state. Though, it can be appreciated that for some embodiments, the sensor(s) may be triggered in such a manner such that the medical device proceeds from the sleep state directly to the activation state without entering into the standby state for a substantial period of time.

In various embodiments, a first time period required for the medical device to transition from the standby state to the fully activated state can be shorter than a second time period required for the medical system to transition from the sleep state to the fully activated state. In other words, the standby state can be a state in which the medical device is prepared to enter the fully activated state quicker than if the medical device had to enter the fully activated state from the sleep state.

Figure 10:
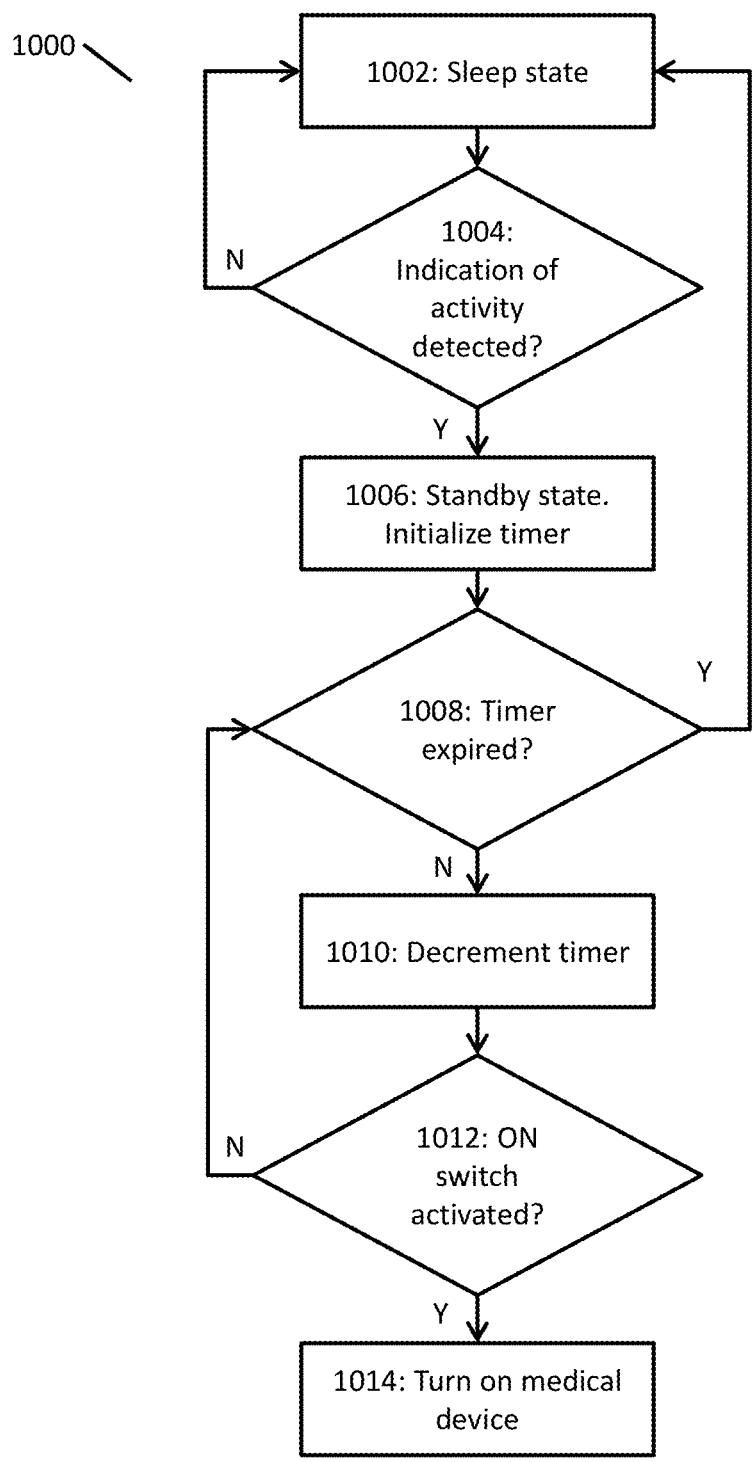
FIG. 10 is a flow-chart depicting an exemplary process for decreasing a time required for a medical device to transition into a fully activated state after an ON button has been activated, according to some embodiments.

FIG. 10 is a flow-chart depicting an exemplary process 1000 where a medical device detects an activity that causes the device to transition from a sleep state to a standby state, and then after being powered on, further transition from the standby state to the fully activated state. In some embodiments, if the medical device is already in the standby state, the time required for the medical device to transition from the standby state into a fully activated state after an ON button has been activated is reduced, according to some embodiments. At stage 1002, the medical device can be in a sleep state. The sleep state can be a state in which one or more components of the medical device, such as one or more processors or their coupled peripherals, are unpowered or un-clocked. The medical device can consume less power in the sleep state than when in the standby state or the fully activated state. Sensors discussed herein may be provided at any appropriate region of the medical device for sensing an activity that initiates transition from a sleep state to standby, pre-rescue mode, power on, and/or any other suitable state. For example, a detected change in motion and/or ambient light at any appropriate part of the medical device may be used for triggering a unit to transition from the sleep state to another more active state.

At stage 1004, the medical device can determine if an indication of activity has been detected. If an indication of activity is detected, the medical device can branch to stage 1006, in which it enters a standby state. Or, for some embodiments, the indication of activity may cause the medical device to proceed directly toward the fully activated state from the sleep state. In such an example, the system may employ varying threshold levels for each transition such that when the system determines that values provided by an activity sensor reaches a first threshold (e.g., degree of acceleration, orientation or velocity of the device), the medical device may transition from a sleep state to a standby state; and when the system determines that the value provided by the activity sensor reaches a second threshold, the medical device may transition from the sleep state directly to the fully activated state. In some embodiments, a series of sensors having suitable threshold levels may be used in combination to determine whether the device should transition to a standby state and/or a fully activated state. For example, an initial acceleration, or other suitable movement may be sufficient to trigger device transition from a sleep state to a standby state, and an additional action, such as removal from a docking station or activation of a power switch/button, may trigger device transition to a more fully activated state. Other activity triggers may be possible, for example, actuation of a mechanical latch/switch, magnetic sensor, light sensor, proximity sensor, amongst others. If no indication of activity is detected, the medical device can remain in the sleep state.

Many types of indications of activity are possible. For example, the medical device can be provided with an accelerometer configured to measure an acceleration of the medical device in one, two, or three axes. The indication of activity can comprise a measured acceleration that exceeds a predetermined acceleration threshold. This can correspond, for instance, with the medical device being taken off a wall or permanent storage space, or moved along with a crash cart used for emergency situations. The medical device can also be configured to calculate a displacement of the medical device based on the measured acceleration. The indication of activity can comprise a measured or calculated displacement that exceeds a predetermined displacement threshold. In some embodiments, the indication of activity can comprise a measured acceleration and/or displacement that exceeds one or more predetermined thresholds in at least two different axes. Requiring measured acceleration and/or displacement in at least two axes can filter out false positives in which the medical device is being transported in a vehicle, but is not yet being used. In these situations where the medical device is being transported but not being used, the medical device can experience acceleration and/or displacement along one axis or, in some cases, multiple axes (e.g., vehicle moving at an incline, decline, and/or turning, etc.). In some embodiments, the indication of activity can also comprise a measured acceleration and/or displacement that exceeds one or more predetermined thresholds in at least three different axes, which can further facilitate filtering out false positives.

In some embodiments, the medical device can also be configured to derive an orientation of the medical device based on an observed acceleration. Alternatively, or in addition, the medical device can also comprise an orientation sensor configured to observe an orientation of the medical device (e.g., whether the medical device is upright, on its side, or upside down). The indication of activity can comprise the medical device detecting a change in orientation, or a transition to a particular orientation (e.g., upright).

Based on the motion and/or orientation of the medical device, for example, as determined by the accelerometer and pre-determined thresholding levels, the device may be triggered to transition from a sleep state to a standby state, or directly to a fully activated state. For example, when the device is placed in a cabinet, in an ambulance, on a shelf, on a crash cart or is otherwise ready (and waiting) for use, once the medical device experiences a sufficient degree of motion (e.g., from being grabbed or transported quickly), the device is automatically turned on to a standby or fully activated state, without requiring direct user interaction. For some embodiments, thresholding levels may be set such that the device is not inadvertently activated due to incidental movement (e.g., a person accidentally bumps into the device) or routine transport (e.g., within a car or on a hospital cart). Or, in some embodiments, the device may be pre-configured such that the appropriate trigger activation applies only when appropriate, for example, when the device is properly situated and ready for use.

In some embodiments, the medical device can also be configured to be connected and disconnected from a power source. For example, the medical device can be configured to be connected to a wall outlet or docking station when not in use, and to be disconnected when it is being transported to a patient for use. In other examples, the medical device can be configured to be disconnected from a power source when not in use, and to be connected to the power source when it is being used. In these embodiments, the medical device can comprise a power sensor configured to determine whether the medical device is connected to the power source. The indication of activity can comprise the medical device detecting that it has been at least one of connected and disconnected to the power source.

In some embodiments, the medical device can comprise a light sensor configured to measure an ambient light level. The indication of activity can comprise the medical device sensing that the ambient light level exceeds a pre-determined light level threshold. An increase in the ambient light level can correspond to the medical device being taken out of a dark storage location or protective covering, and can indicate that the medical device is about to be activated.

In some embodiments, the medical device can comprise an ultrasound, infrared, radio, or other proximity sensor configured to measure a distance between the medical device and a neighboring surface, such as a wall. The indication of activity can comprise the medical device detecting a change in the measured distance. An increase in the measured distance can correspond to the medical device being taken out of or moved along with a storage location (e.g., wall cabinet, crash cart) and being prepared for use.

In various embodiments, the medical device may include sensors for detecting whether the electrodes have been removed and/or opened, which may be employed as an activity that triggers the medical device to transition from the sleep state to a pre-rescue mode, and/or standby state. For example, an infrared emitter and sensor may be provided on either side of the electrode holster portion and unit backing. When remaining in the holster, the electrodes block transmission of infrared light there through; hence, when the electrodes are situated in the holster, the infrared sensor is unable to detect the infrared light from the emitter. However, when the electrodes are removed from the holster, the sensor is able to detect the emitted infrared light. Once the sensor detects the infrared light, as an indication that the electrodes have been removed and that the medical device should be activated, transition from the sleep state can occur. In some embodiments, the electrode packaging may be configured to trigger the medical device transition from sleep state to a pre-rescue mode or standby state upon opening thereof, for example, in case removal of the packaging from the holster does not trigger the transition. For example, the packaging may include a shorting mechanism that causes such a transition.

In another embodiment, the medical device may employ a Hall effect sensor, which varies its output voltage in response to a magnetic field. For example, the medical device may include a magnetic sensor (e.g., located on the circuit board, handle, or other suitable location) and the electrode packaging may include a magnet. When the package is seated in the holster, the magnet and sensor may be situated close enough to remain within a predetermined "trip" distance threshold, which causes the circuitry to remain open, so as not to transition from the sleep state to the pre-rescue mode, or standby state. Though, when the magnet is moved far enough away from the magnetic sensor, exceeding a predetermined "release" distance threshold, the circuit may close and provide an indication that the electrode package is removed. In some embodiments, the "trip" and "release" distance threshold values of the sensor may be different, with the "release" distance value exceeding the "trip" distance value. Therefore, if the package moves around slightly within the holster but is not fully removed, then the chance of a false positive occurrence is relatively low.

In some embodiments, the medical device can comprise a handle, and at least one capacitance sensor configured to measure a capacitance associated with the handle. The indication of activity can comprise the medical device detecting a capacitance from the capacitance sensor consistent with the handle being grasped by a human hand. This can correspond to the medical device being handled by a human operator, and can indicate that the device is about to be activated.

In certain embodiments, the medical device may be activated to an appropriate state by the action of a user in grasping the handle of the device. For instance, the handle of the medical device may include one or more sensing devices, for example, a mechanical switch, a magnet and inductor combination, a magnet and a reed switch, a flex sensor, and/or any other suitable sensor(s) for detecting a threshold amount of force or other activity associated with the handle sufficient to cause the medical device to activate. Such sensing devices may be incorporated with a handle of the device, or other region that is intended to be grasped by the user. For example, the sensing device(s) may be implemented at a mechanical transition point, such as where the handle attaches to the housing of the medical device. That way, when the handle is gripped, pulled and/or lifted by a user, the force associated with such an action is most likely to be transferred through the sensor. Accordingly, the sensor is in a suitable position to detect forces experienced by the handle sufficient to trigger the device to enter into a more activated state (e.g., power on, standby, pre-rescue, fully active).

A flex sensor exhibits a variable resistance depending on the degree to which the flex sensor is bent or flexed. In the case of a flex sensor, as known to those of skill in the art, the resistance through the flex sensor will vary (e.g., increase, decrease) as it experiences bending. Accordingly, a handle incorporating a flex sensor may be able to provide information for detecting whether the handle has been grasped by a user. For instance, the handle may be grasped in a manner that causes the flex sensor to bend a sufficient degree to exhibit a noticeable change in resistance (albeit, employing a slight amount of current through the sensor to measure such a change). This change in resistance may be trigger the medical device to be appropriately activated.

In an embodiment that employs a magnet switch including a magnet and inductor (e.g., inductor coil). The magnet may be attached to the handle, and the inductor may be attached to another part of the medical device, such as the housing, or vice versa, the inductor may be attached to the handle and the magnet may be attached at another location. When the handle is grasped so as to cause the magnet to sweep across the inductor with a sufficient velocity (e.g., exceeding a threshold), the inductor will generate an electrical pulse that may act as a trigger for the medical device to activate. In another example, the medical device may include an inductor and the electrode packaging may include a magnet, or vice versa, the medical device may include a magnet and the electrode packaging may include an inductor. As the electrode package is removed from the holder and sweeps the magnet across the inductor, an electrical pulse could be generated to signify the package has been removed from the storage location. The electrical pulse could provide an indication of the activity and transition the device into the appropriate active state. An advantage to using such a magnet and inductor combination is that it requires no external power source in its operation.

Similarly, a magnet and reed switch may be employed as a magnet switch implementation. As understood by those skilled in the art, a reed switch involves an electrical switch operated by a magnetic field. As an example, a reed switch may include two or more magnetizable, flexible, conductive reeds hermetically sealed within a container (e.g., glass envelope) having end portions separated by a small gap when the switch is open. Exposure to a magnetic field causes the reeds to come together, closing the electrical circuit. The reeds may have a stiffness such that the reeds elastically separate when the magnetic field is removed, re-opening the electrical circuit. Or conversely, the reed switch may be constructed such that the electrical circuit is normally closed when not exposed to a magnetic field, and closed when exposed to the magnetic field. Similar to other embodiments, the magnet may be attached to the handle, and the reed switch may be attached to another part of the medical device, such as the housing, or vice versa, the reed switch may be attached to the handle and the magnet may be attached at another location. When the handle is grasped so as to cause the reed switch to be exposed to the magnetic field of sufficient strength (e.g., exceeding a threshold), the reed switch will close (or open), acting as a trigger for the medical device to activate. As another example, the medical device may include a reed switch and the electrode packaging may include a magnet, or vice versa, the medical device may include a magnet and the electrode packaging may include a reed switch. While the electrode packaging is situated within the device holster, the magnet may remain within range of the reed switch keeping the circuit element closed. As the electrode packaging is removed the reed switch may become open, indicating the removal of the electrode packaging and trigger the device to transition from the sleep state to a pre-rescue mode, and/or standby state. The reed switch may also be situated such that the circuit element remains open as the electrode packaging remains within the holster but the magnet is out of range (i.e. unable to close the switch). As the electrode package is removed it could come within range to close the reed switch, and then move out of range as the packaging continues to be removed, thus re-opening the switch. Similar to other embodiments, such a magnet and reed switch combination requires no external power source in its operation.

A simple mechanical switch may also be incorporated in the handle of the device. For example, the switch may be placed at a mechanical transition point where force associated with grasping of the handle is transferred there through. In such a case, the switch would be triggered when a user pulls the handle which may, in turn, cause the medical device to activate. Similar to the magnet and inductor arrangement, this particular implementation also does not require an external power source for activation to occur.

In some embodiments, the medical device may employ a communication interface between electrical components. For example, the device could contain a passive Near Field Communication (NFC) circuit and the electrode could contain an active NFC circuit. While the active NFC circuit (e.g., electrodes) is situated within the holster, and within range of the passive NFC circuit, the device will be able to detect (e.g., through the electrodes) the presence of the electrodes. Once removed from the holster the active NFC circuit will exceed the communication distance to the passive NFC circuit so as to indicate the removal of the pads from the device. The active and passive elements, or any combination thereof, could be used to detect the presence of the electrodes within the holster. As another example, the device could utilize RFID or low powered Bluetooth, e.g., to determine the signal strength between the device and electrode set. The signal strength could be used as a distance identifier to determine whether or not the electrodes are within the device holster.

If the medical device detects an appropriate indication of activity, the medical device can transition to stage 1006, in which the medical device can enter a standby state. As described above, the standby state can be any state in which the medical device can transition into a fully activated state faster than if the medical device had to transition into the fully activated state from the sleep state. In some but not all embodiments, the medical device can consume more power, and/or be associated with a shorter Mean Time Before Failure (MTBF) as compared to the sleep state. While in the standby state, the medical device can provide power to or turn on clocks associated with one or more components of the medical device, such as one or more processors and/or connected peripherals. The medical device can also load needed software from non-volatile data storage 104 into volatile memory 116.

Accordingly, for some embodiments, the device may be automatically powered on into an appropriate state (e.g., standby, pre-rescue, fully active, etc.) for the rescuer without requiring a rescuer or other operator to manually push the power button or wait until a different activity (e.g., threshold motion of the device) is triggered, thus, reducing overall rescue time. In some instances, when transitioned from a sleep state to a pre-rescue or standby state, the device may prompt the rescuer to carry out one or more resuscitation-related activities. For example, the device may prompt the rescuer to take the defibrillator to the patient, press the power button (e.g., located in an upper left or right hand corner), and/or provide other instructive feedback. Such prompting may include, for example, audio instruction to carry out the activities and/or display of one or more images on the user interface screen (e.g., person/finger pressing the power button or with an arrow pointing to the power button). In some embodiments, removal or opening of the electrode packaging may trigger a signal to be sent to volatile memory 116 to indicate that the step of removing the electrodes has already been completed. Accordingly, the prompts provided to the rescuer may be truncated (e.g., skipping over prompts for steps that have already been completed) so as to reduce the total amount of time required to carry out the overall resuscitation protocol. Hence, the total amount of annunciated or given instruction prompts may be reduced. Such a feature may decrease the total rescue time by eliminating redundancy in the system that would otherwise cause the user to wait for instruction prompts to be issued for activities that have already been completed.

While transitioning from the sleep state to either the standby or fully activated state, the medical device can also conduct any of the steps described above in relation to FIGS. 5-8, including conducting one or more tests on the functionality of various operational circuits, and/or reporting on the results of said tests. In one exemplary embodiment, the medical device can implement tests on the functionality of various hardware and software modules as described above, but not activate said hardware or software modules, while in the standby state and/or while transitioning to the fully activated state. In another exemplary embodiment, the medical device can power-on volatile memory 116 and optionally begin loading instructions from non-volatile data storage 104 into volatile memory 116, but not yet power-on other peripheral devices, such as other components depicted in FIG. 1. In yet other embodiments, the medical device can begin providing power to various components, such as any of the components depicted in FIG. 1, but not yet provide a clock signal (or perhaps provide a slower clock signal). By providing power but not a clock signal (or a slower clock signal), the medical device can prepare these various components for a quick startup while still consuming less power than if the components were both powered and clocked. The standby state, or any other state leading up to the fully activated state, can be any state in which the medical device can transition into a fully activated state faster than if the medical device had to transition into the fully activated state from a sleep state, and is not limited to any of the exemplary embodiments described above. Also as part of stage 1006, the medical device can initialize a timer. The timer can be loaded with a pre-determined duration for which the medical device will remain in the standby state.

At stage 1008, the medical device can determine if the timer has expired. If the timer has expired, process 1000 can branch back to stage 1002, in which the medical device returns to the sleep state. If the timer has not expired, process 1000 can branch to stage 1010, in which the timer is decremented. After the timer is decremented, process 1000 can branch to stage 1012.

At stage 1012, process 1000 can evaluate whether an ON switch associated with the medical device has been activated. If the ON switch has not been activated, the process 1000 can return to stage 1008. If the ON switch has been activated, process 1000 can transition to stage 1014, in which the medical device transitions to the fully activated state. In some embodiments, the fully activated state can be any state in which the medical device can perform more functions than while in the standby state or in the sleep state. In some embodiments, the fully activated state can also be any state in which the medical device consumes more power compared to the standby state or the sleep state. In some embodiments, the fully activated state can also be any state associated with a shorter Mean Time Before Failure (MTBF) as compared to the standby state or the sleep state. To transition to the fully activated state, the medical device can turn on additional components as compared to the standby state or the sleep state, including turning on any of the components depicted in FIG. 1. The medical device can also turn on or increase clock speeds to various components in the medical device that were previously powered but left un-clocked, or clocked at a lower clock speed. The medical device can also load additional software instructions, modules or data while in the fully activated state as compared to the standby state or the sleep state.

As previously mentioned, in some embodiments, the medical device can consume more power while in the fully activated state than while in the standby state. Also in some embodiments, the fully activated state can be associated with a shorter MTBF as compared to the standby state or the sleep state. It can therefore be advantageous to minimize the amount of time that the medical device spends in the fully activated state during its operational lifetime, while at the same time allowing the medical device to turn on quickly when needed. Process 1000 can facilitate this by implementing a standby state if an indication of activity is detected. If the ON switch is subsequently actuated, the medical device can transition into the fully activated state faster than if the medical device had been in the sleep state.

While process 1000 has been described as a sequential series of steps, in actual operation process 1000 can be implemented using an interrupt-based approach. For instance, a component of the medical device, such as an autonomous or semi-autonomous controller or Application Specific Integrated Circuit (ASIC) can be configured to continuously monitor for an indication of activity. If the indication of activity, is detected, the component can generate an interrupt. If the one or more processors of the medical device (e.g., processor 122) is asleep when the interrupt is generated, the interrupt can cause the one or more processors to wake up (e.g., by turning on the processor's power and/or turning on the processor's clock) and to implement the steps needed to transition into a standby state. Similarly, a component of the medical device can also be configured to continuously monitor the ON switch. If the ON switch is activated, the component can also generate an interrupt. The interrupt can also cause the one or more processors to transition into the fully activated state. In such embodiments, the medical device can continuously monitor for indications of activity and/or activation of the ON switch, rather than only when process 1000 reaches stage 1004 and/or stage 1012.

FIG. 11A is a side view of an exemplary defibrillator device 1100 that can embody the components, features, and processes described above, according to some embodiments. FIG. 11 B is a top view of the same exemplary defibrillator device 1100, according to some embodiments. Device 1100 can include a handle 1102 disposed at or near the top of the device, and which is configured to be grasped by a human hand. Device 1100 can also include side sensors 1104a and 1104b and/or top sensors 1106a and 1106b which can be configured to detect whether electrodes stored in holster slots 1101 adjacent to said sensors have been removed. As discussed above, for example, sensors 1104a and 1104b, and/or sensors 1106a and 1106b can comprise an infrared emitter and sensor provided on either side of the electrode holster portion and unit backing. When remaining in the holster 1101, the electrodes block transmission of infrared light there through; hence, when the electrodes are situated in the holster 1101, the infrared sensor is unable to detect the infrared light from the emitter. However, when the electrodes are removed from the holster 1101, the sensor is able to detect the emitted infrared light. Once the sensor detects the infrared light, as an indication that the electrodes have been removed and that the medical device should be activated, transition from the sleep state can occur. Alternatively, or in addition, sensors 1104a, 1104b, 1106a, and/or 1106b can comprise magnetic sensors configured to detect the presence of magnets disposed on the electrodes, also as discussed above.

Figure 11C:
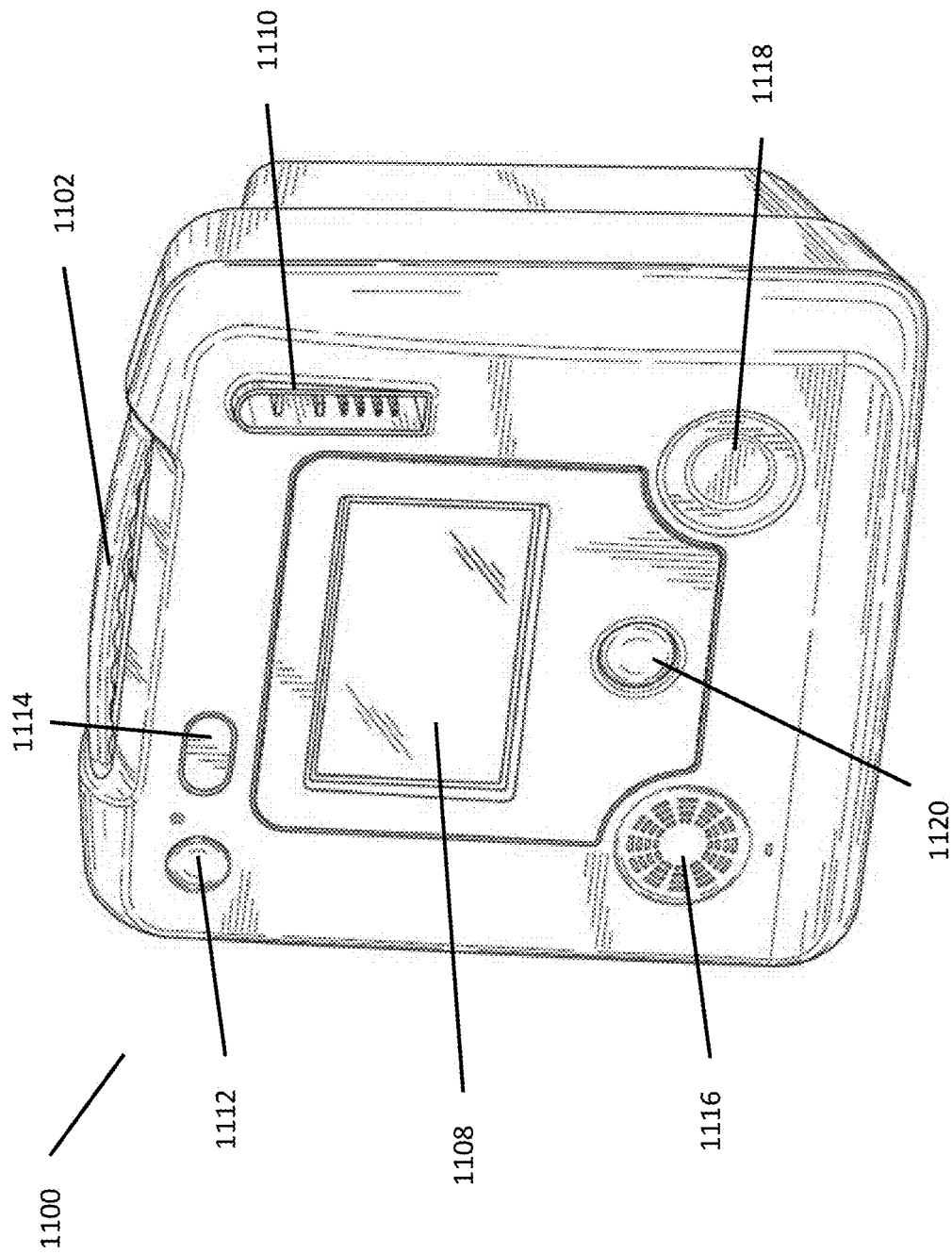

FIG. 11C is a front view of the same exemplary defibrillator device 1100. In addition to handle 1102, the device 1100 can also include a screen 1108, a connector socket 1110, a power button 1112, a status indicator 1114, a speaker 1116, a pediatric/adult mode button 1118, and a shock button 1120. The screen 1108 can be configured to display the images and text described above as well as instructions for a user to administer resuscitative therapy, while the speakers 1116 can be configured to play the audio prompts described above. The connector socket 1110 may be configured to receive a connector for a set of electrodes and/or CPR sensors to be connected to the defibrillator. The pediatric/adult mode button 1118 may provide the ability to toggle between adult and pediatric mode configurations of the defibrillator, and may further include an indicator (not shown in the figure) for showing to a user what state or mode the device is currently operating in. Depending on whether the defibrillator is in adult or pediatric operating modes, the defibrillator may provide different functions. For example, the overall level of defibrillating energy, the manner in which user instructions are provided and/or the type of ECG analysis may vary based on whether the defibrillator is set to adult or pediatric operating modes.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical system comprising:
   a plurality of operational circuits comprising at least one therapy delivery device;
   at least one processor coupled to the plurality of operational circuits, the at least one processor configured to:
   initiate, when the medical system is activated, a boot process for the medical system, wherein the boot process comprises a first phase and a second phase, wherein the first phase is executed prior to the second phase;
   execute, as part of the first phase of the boot process, a first set of tests configured to test functionality of one or more operational circuits of the plurality of operational circuits, the one or more operational circuits comprising the at least one therapy device;
   provide, based on the first set of tests, an indication regarding usability as an assurance to a user that the medical system is working properly prior to completion of the boot process; and
   after implementing the first set of tests, execute the second phase of the boot process.

2. The medical system of claim 1, wherein the at least one processor is capable of executing multiple process threads, and the first phase does not trigger the execution of multiple process threads, and the second phase triggers the execution of multiple process threads.

3. The medical system of claim 2, wherein the first phase does not trigger the execution of multiple process threads, and the second phase triggers the execution of multiple process threads.

4. The medical system of claim 1, wherein the at least one processor is further configured to execute, as part of the second phase of the boot process, a second set of tests configured to test the functionality of the one or more operational circuits of the plurality of operational circuits.

5. The medical system of claim 4, wherein:
   the plurality of operational circuits comprises a battery; and
   the second set of tests comprises a test on a functionality of the battery.

6. The medical system of claim 1, wherein:
   the at least one processor comprises a first processor and a second processor, the first processor including a processor core.

7. The medical system of claim 6, wherein:
   the first processor is configured to implement a general purpose operating system; and
   the second processor is configured to implement a real-time operating system.

8. The medical system of claim 6, wherein the processor core is configured to execute the first set of tests by fetching a result of a self-test conducted by the second processor.

9. The medical system of claim 1, wherein the first set of tests include a power on self-test conducted by the at least one processor.

10. The medical system of claim 1, wherein:
    the therapy delivery device comprises a defibrillator circuit configured to deliver a therapeutic electric shock to a patient; and
    the first set of tests comprises a test on the defibrillator circuit.

11. The medical system of claim 10, wherein:
    the plurality of operational circuits comprises an input circuit configured to instruct the defibrillator circuit to deliver the therapeutic electric shock; and
    the first set of tests comprises a test on the input circuit.

12. The medical system of claim 10, further comprising a defibrillator housing, the defibrillator housing containing the plurality of operational circuits.

13. The medical system of claim 1, wherein:
    the plurality of operational circuits comprises an inter-component communication circuit associated with a communication circuit driver; and
    the at least one processor is configured to execute the first set of tests by utilizing the inter-component communication circuit before loading the associated communication circuit driver.

14. The medical system of claim 13, wherein the inter-component communication circuit is at least one of an Inter-Integrated Circuit (12C) and a Universal Asynchronous Receiver/Transmitter (UART).

15. The medical system of claim 1, wherein:
    the plurality of operational circuits comprises a user interface output device associated with an output device driver; and
    the at least one processor is configured to report results associated with the first set of tests by utilizing the user interface output device before loading the output device driver.

16. The medical system of claim 15, wherein the user interface output device provides the indication regarding usability of the medical system prior to the completion of the boot process.

17. The medical system of claim 15, wherein the user interface output device is at least one of an audio speaker and a video display.

18. The medical system of claim 17, wherein the video display is configured to display an initial image to provide the indication regarding usability of the medical system prior to the completion of the boot process.

19. The medical system of claim 17, wherein the audio speaker is configured to announce a prompt to provide the indication regarding usability of the medical system prior to the completion of the boot process.

* * * * *

UNITED STATES PATENT AND TRADEMARK OFFICE
CERTIFICATE OF CORRECTION

PATENT NO. : 10,561,852 B2
APPLICATION NO. : 15/433047
DATED : February 18, 2020
INVENTOR(S) : Jim Murphy et al.

Page 1 of 1

It is certified that error appears in the above-identified patent and that said Letters Patent is hereby corrected as shown below:

On the Title Page

Item (72), please correct the name of the fifth inventor from:
"Tim Stever"
To:
--Timothy F. Stever--

Signed and Sealed this
Fourteenth Day of April, 2020

Andrei Iancu
*Director of the United States Patent and Trademark Office*